US009610076B2

(12) United States Patent
Melsheimer et al.

(10) Patent No.: US 9,610,076 B2
(45) Date of Patent: Apr. 4, 2017

(54) WOUND CLOSURE DEVICE

(71) Applicant: Cook Medical Technologies LLC, Bloomington, IN (US)

(72) Inventors: Jeffry S. Melsheimer, Springville, IN (US); Edwin Macatangay, Bloomington, IN (US); Bradley Foulke, Bloomington, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 379 days.

(21) Appl. No.: 14/181,034

(22) Filed: Feb. 14, 2014

(65) Prior Publication Data

US 2014/0236189 A1   Aug. 21, 2014

Related U.S. Application Data

(60) Provisional application No. 61/765,264, filed on Feb. 15, 2013.

(51) Int. Cl.
*A61B 17/04* (2006.01)
*A61B 17/00* (2006.01)
*A61B 17/062* (2006.01)
*A61B 17/06* (2006.01)

(52) U.S. Cl.
CPC ...... *A61B 17/0469* (2013.01); *A61B 17/0057* (2013.01); *A61B 17/0625* (2013.01); *A61B 2017/00663* (2013.01); *A61B 2017/047* (2013.01); *A61B 2017/0472* (2013.01); *A61B 2017/06076* (2013.01)

(58) Field of Classification Search
CPC . A61B 17/04; A61B 17/0057; A61B 17/0469; A61B 17/0625; A61B 2017/00663; A61B 2017/047; A61B 2017/0472; A61B 2017/06076
USPC ........................................................ 606/144
See application file for complete search history.

(56) References Cited

U.S. PATENT DOCUMENTS

| | | | |
|---|---|---|---|
| 4,641,652 A | 2/1987 | Hutterer | |
| 5,176,691 A | 1/1993 | Pierce | |
| 5,356,424 A | 10/1994 | Buzerak | |
| 5,417,699 A | 5/1995 | Klein | |
| 5,591,179 A | 1/1997 | Edelstein | |
| 5,713,910 A * | 2/1998 | Gordon | A61B 17/0482 112/169 |
| 5,810,851 A | 9/1998 | Yoon | |
| 5,820,631 A | 10/1998 | Nobles | |
| 6,626,917 B1 | 9/2003 | Craig | |
| 2006/0036265 A1 | 2/2006 | Dant | |
| 2009/0240264 A1* | 9/2009 | Tuval | A61B 17/0469 606/148 |
| 2010/0094411 A1* | 4/2010 | Tuval | A61F 2/2418 623/2.1 |

(Continued)

*Primary Examiner* — Eric Rosen
*Assistant Examiner* — George J Ulsh
(74) *Attorney, Agent, or Firm* — Brinks Gilson & Lione

(57) ABSTRACT

A device is provided for closing a wound, such as a percutaneous access site. The device is inserted into the wound, and a helically shaped pusher is actuated to penetrate a wall of the wound. The pusher extends a suture through the tissue wall. After the suture is extending through the tissue wall, the pusher is retracted out of the tissue, while the suture remains extending through the tissue. The suture may then be used to close the wound.

18 Claims, 24 Drawing Sheets

(56) References Cited

U.S. PATENT DOCUMENTS

2012/0089159 A1 4/2012 Shluzas
2012/0271322 A1 10/2012 Mohamed

* cited by examiner

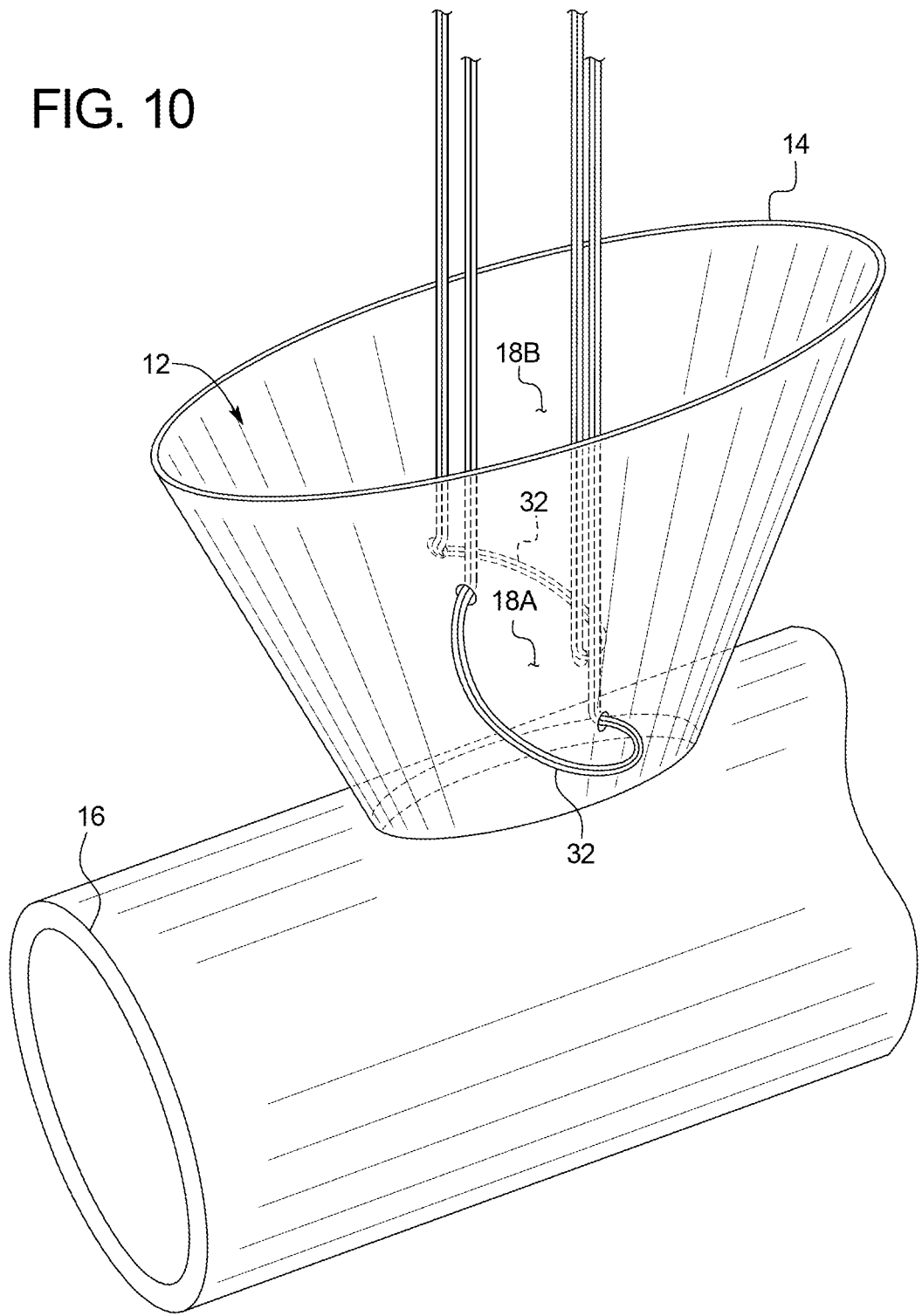

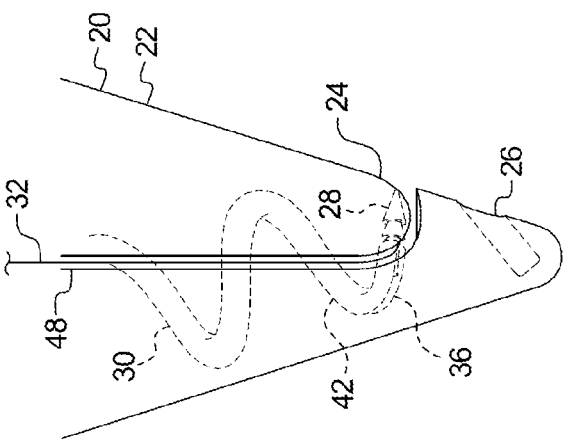
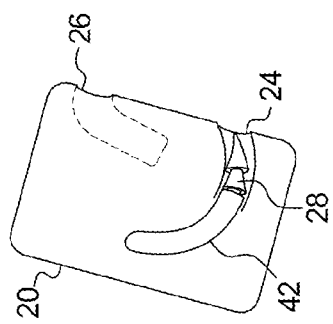
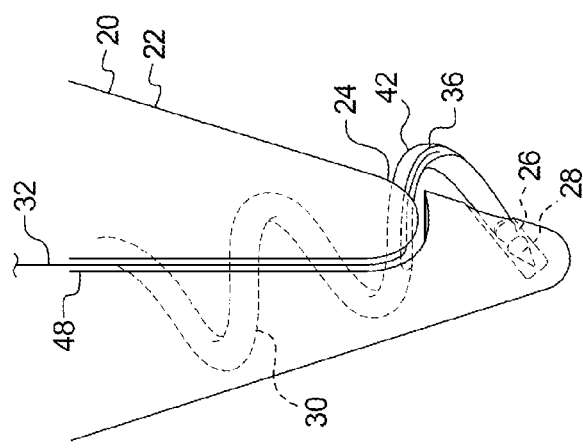
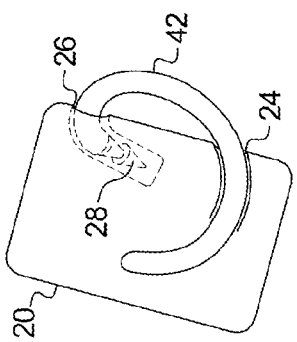
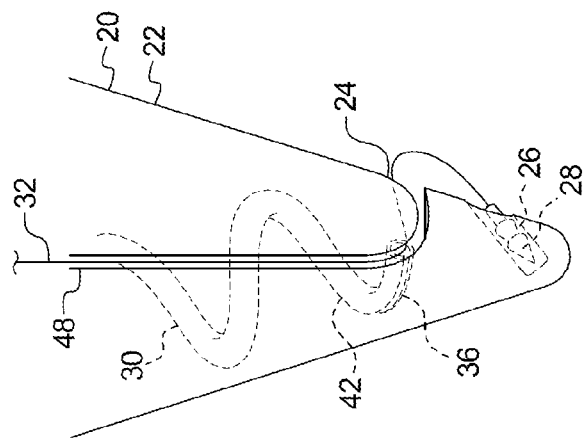
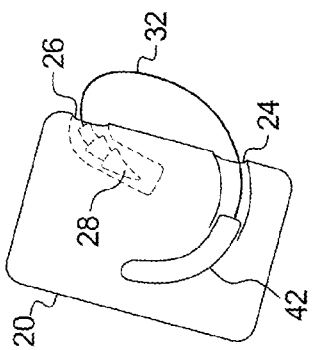

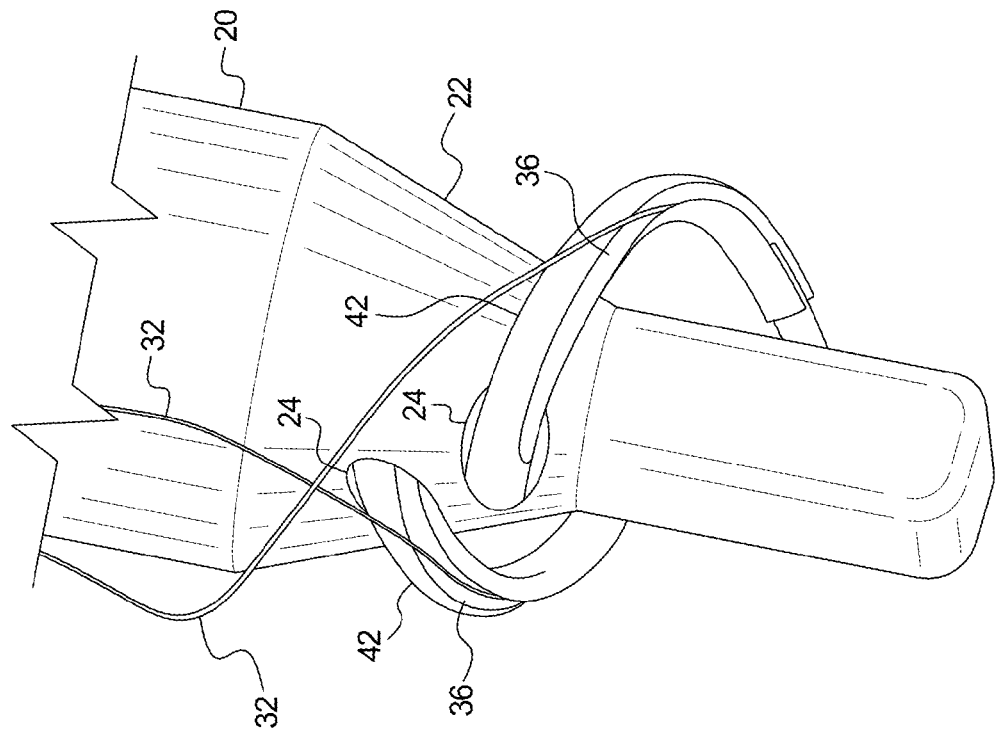
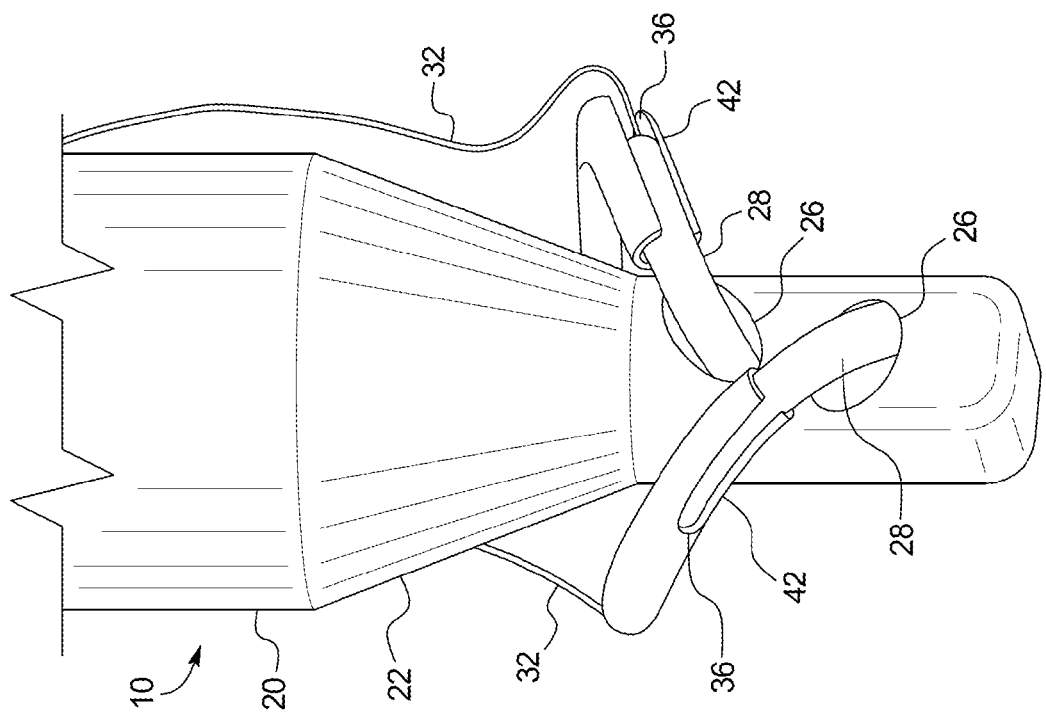

WOUND CLOSURE DEVICE

This application claims priority to U.S. Provisional Application No. 61/765,264, filed Feb. 15, 2013, which is hereby incorporated by reference herein.

BACKGROUND

The present invention relates generally to medical devices and more particularly to a device for closing a wound, such as a percutaneous access site.

Minimally invasive medical procedures have become common in the medical profession due to the lower risk and trauma associated with minimally invasive procedures and the lower cost compared to open surgical procedures. Minimally invasive procedures generally involve gaining access to an organ of a patient by puncturing the patient's skin, intermediate tissues between the skin and the organ, and the wall of the organ. An elongate medical instrument may then be inserted through the access site so that the distal end of the medical instrument is located within the patient's internal anatomy, while the proximal end of the medical instrument remains outside the patient's body. The physician may then manipulate the proximal end of the medical instrument outside the patient's body to move and orient the distal end of the medical instrument to a location within the vessel where treatment is needed. Thus, an internal treatment site within a patient's anatomy may be treated from outside the patient's body through a relatively small access site that is located some distance from the treatment site. By contrast, conventional open surgical procedures would require opening the tissues immediately adjacent the treatment site so that the surgeon can gain direct access to the treatment site.

After a minimally invasive procedure is completed, the elongate medical instrument and related devices are removed from the patient through the access site. However, at the conclusion of the procedure, an open percutaneous wound is left at the access site. Typically, percutaneous wounds created during minimally invasive procedures are closed using a staple, suture or other permanent or semi-permanent implantation, or by using direct pressure to provide hemostasis. Although conventional wound closure devices exist, the inventor believes it would be desirable to provide an improved wound closure device that uses a suture to close a wound.

SUMMARY

A wound closure device is described. The wound closure device has a helically-shaped pusher that pushes a suture through body tissue. After the pusher penetrates the body tissue, the pusher is retracted back through the body tissue. However, the suture remains extending through the body tissue after the pusher is retracted. The wound closure device may then be removed, and the suture may be used to close the wound. The inventions herein may also include any other aspect described below in the written description, the claims, or in the attached drawings and any combination thereof.

BRIEF DESCRIPTION OF SEVERAL VIEWS OF THE DRAWINGS

The invention may be more fully understood by reading the following description in conjunction with the drawings, in which:

FIG. 10 is a plan view of the method of closing a wound, showing the wound closure device removed and two suture portions extending through generally opposite walls of the wound;

FIG. 21 is a plan view of the wound closure device, showing the pusher prior to actuation;

FIG. 22 is a sectional view of the wound closure device of FIG. 21;

FIG. 23 is a plan view of the wound closure device, showing the pusher after actuation;

FIG. 24 is a sectional view of the wound closure device of FIG. 23;

FIG. 25 is a plan view of the wound closure device, showing the pusher retracted and the sharp tip remaining in the second port of the housing;

FIG. 26 is a sectional view of the wound closure device of FIG. 25;

FIG. 27 is a plan view of another embodiment of a wound closure device, showing two pushers actuated and the sharp tips received by the second ports;

FIG. 28 is a plan view of the wound closure device of FIG. 27, showing the two pushers actuated and extending from the first ports;

DETAILED DESCRIPTION

Figure 1:
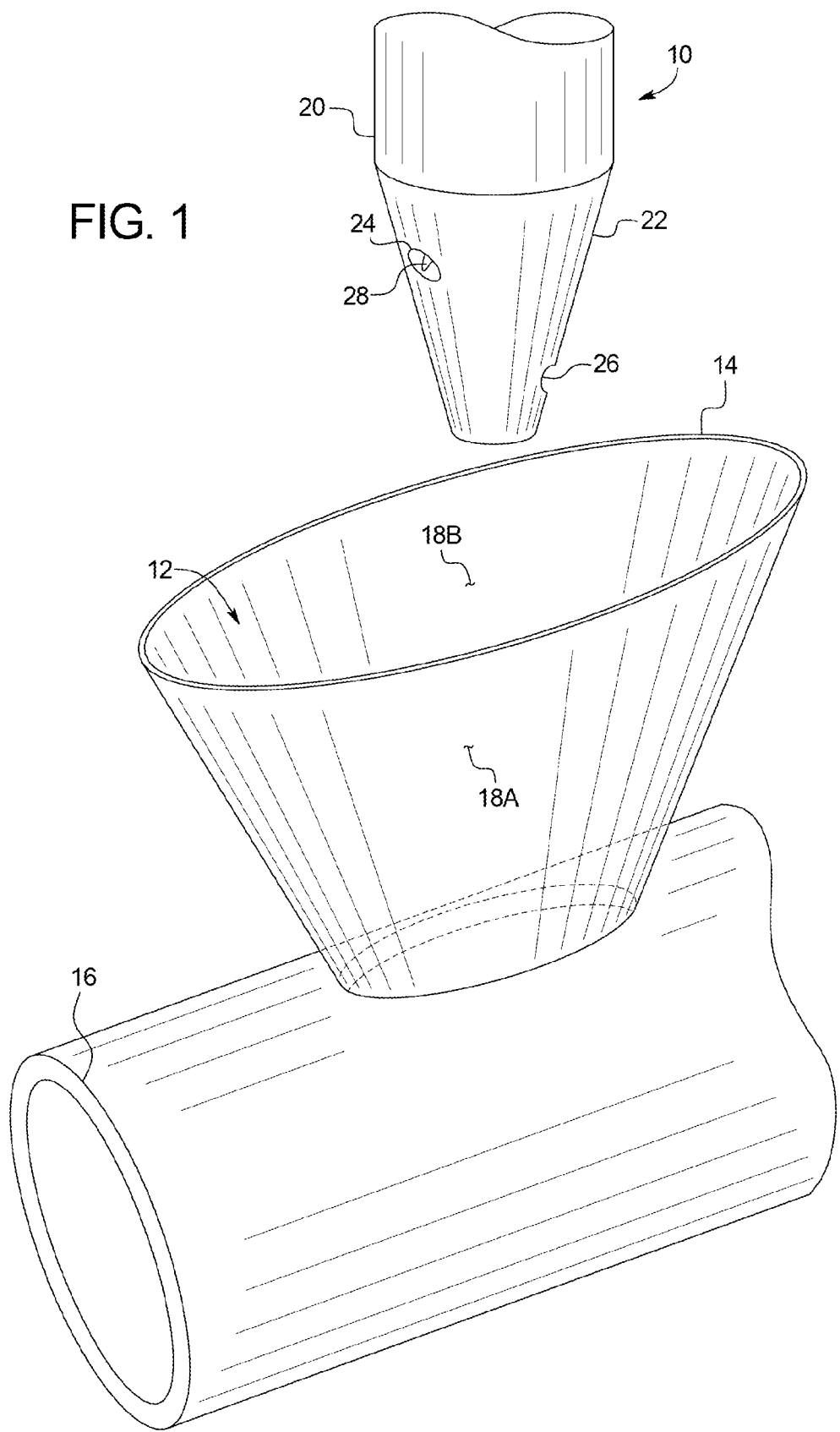
FIG. 1 is a plan view of a method of closing a wound, showing a wound closure device prior to insertion into the wound.
Figure 11:
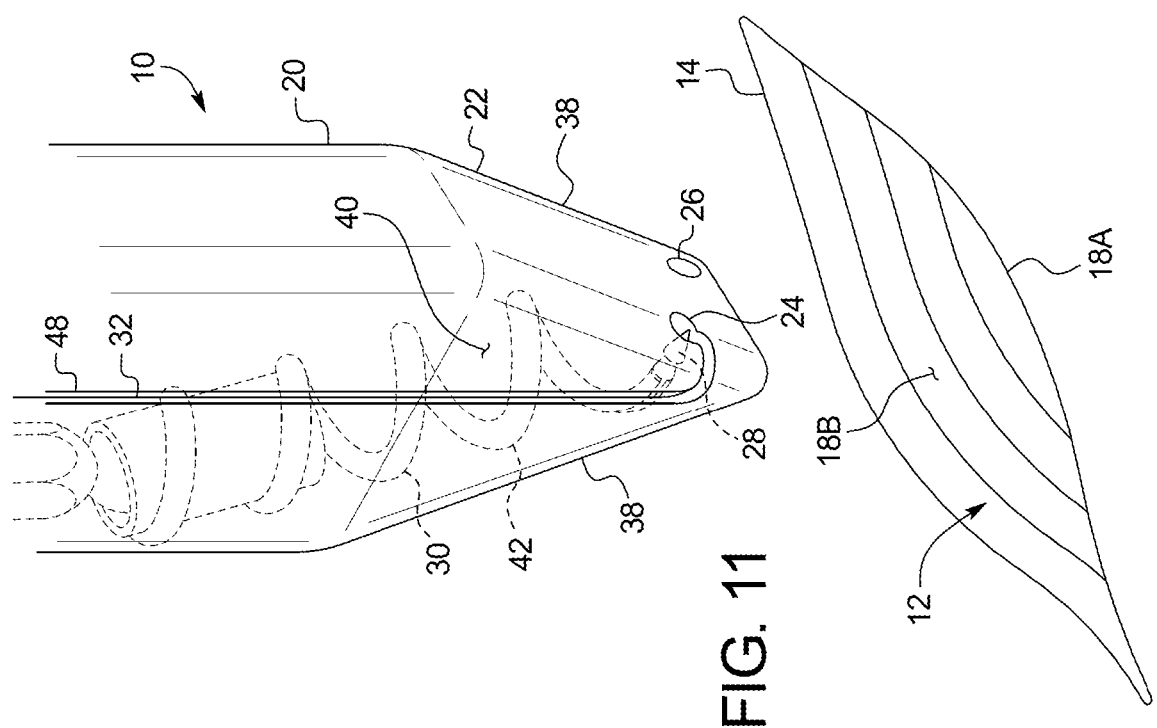
FIG. 11 is a plan view of another embodiment of a wound closure device, showing the wound closure device prior to insertion into the wound.
Figure 13:
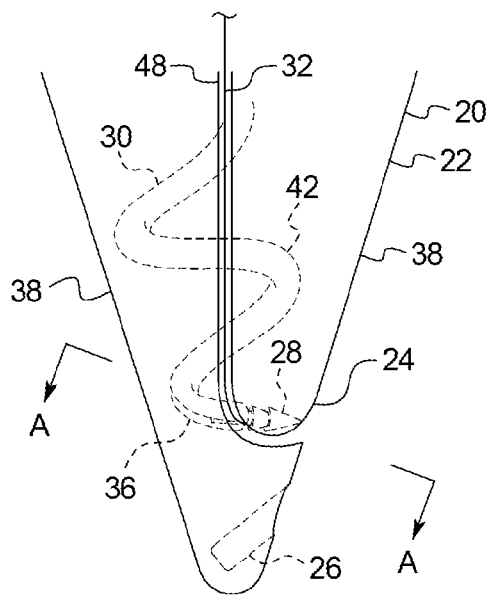
FIG. 13 is a plan view of the wound closure device, showing the pusher prior to actuation.
Figure 15:
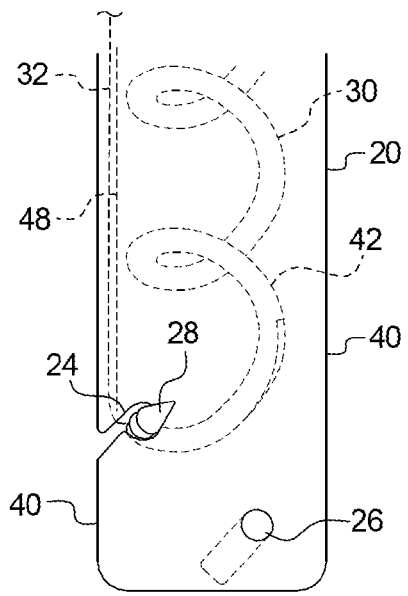
FIG. 15 is a plan view of the wound closure device oriented 90° from the view of FIG. 13.
Figure 14:
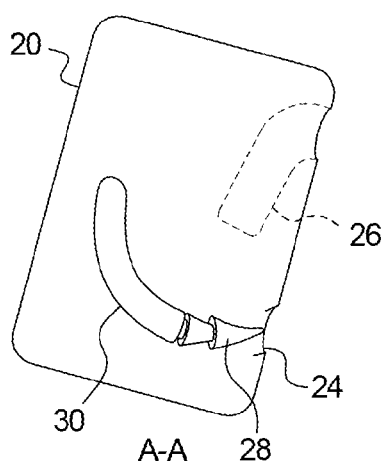
FIG. 14 is a sectional view of the wound closure device of FIG. 13.
Figure 16:
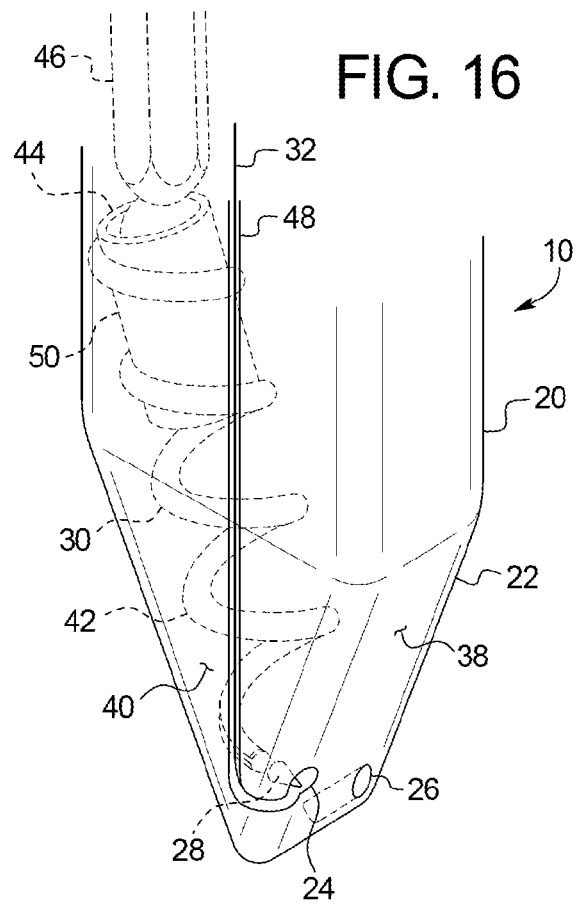
FIG. 16 is a perspective view of the wound closure device of FIG. 13.
Figure 17:
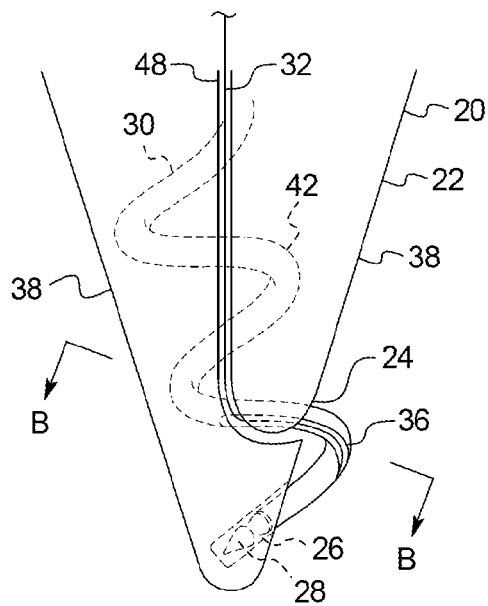
FIG. 17 is a plan view of the wound closure device, showing the pusher after actuation.
Figure 19:
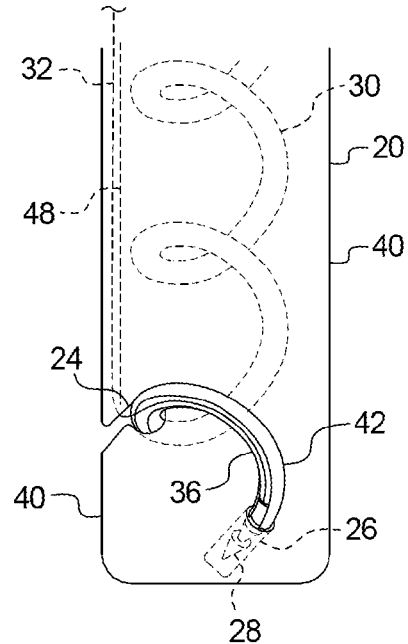
FIG. 19 is a plan view of the wound closure device oriented 90° from the view of FIG. 17.
Figure 18:
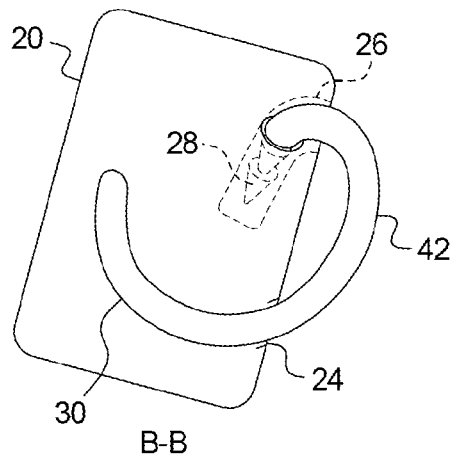
FIG. 18 is a sectional view of the wound closure device of FIG. 17.
Figure 20:
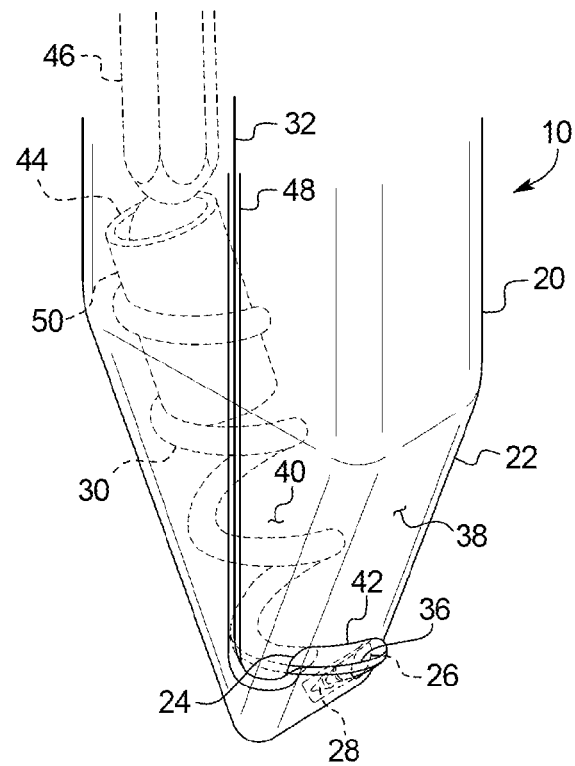
FIG. 20 is a perspective view of the wound closure device of FIG. 17.

Referring now to the figures, and particularly to FIGS. 1-10, a wound closure device 10 is shown for closing a wound 12, such as a percutaneous access site 12. As shown, the wound 12 extends from a patient's skin 14 through underlying tissues and through an internal artery 16. Although the wound 12 may have various shapes, depths and widths, the wound 12 will generally have some form of opposing walls 18A, B of the body tissue. In FIG. 1, the wound closure device 10 is shown above the wound opening prior to being inserted into the wound 12. As shown, the wound closure device 10 may have a housing 20 with a tapered portion 22 along the distal end. Although the tapered portion 22 may have a conical shape as shown in FIG. 1, the tapered portion 22 may also have tapered flat surfaces 38 interconnected by flat surfaces 40 as shown in FIG. 11. As further shown and described below, the housing 20 may also have a first port 24 and a second port 26 that are longitudinally and circumferentially spaced apart from each other. As shown in FIG. 1, the first and second ports 24, 26 may both be located along the tapered portion 22 if desired.

Figure 2:
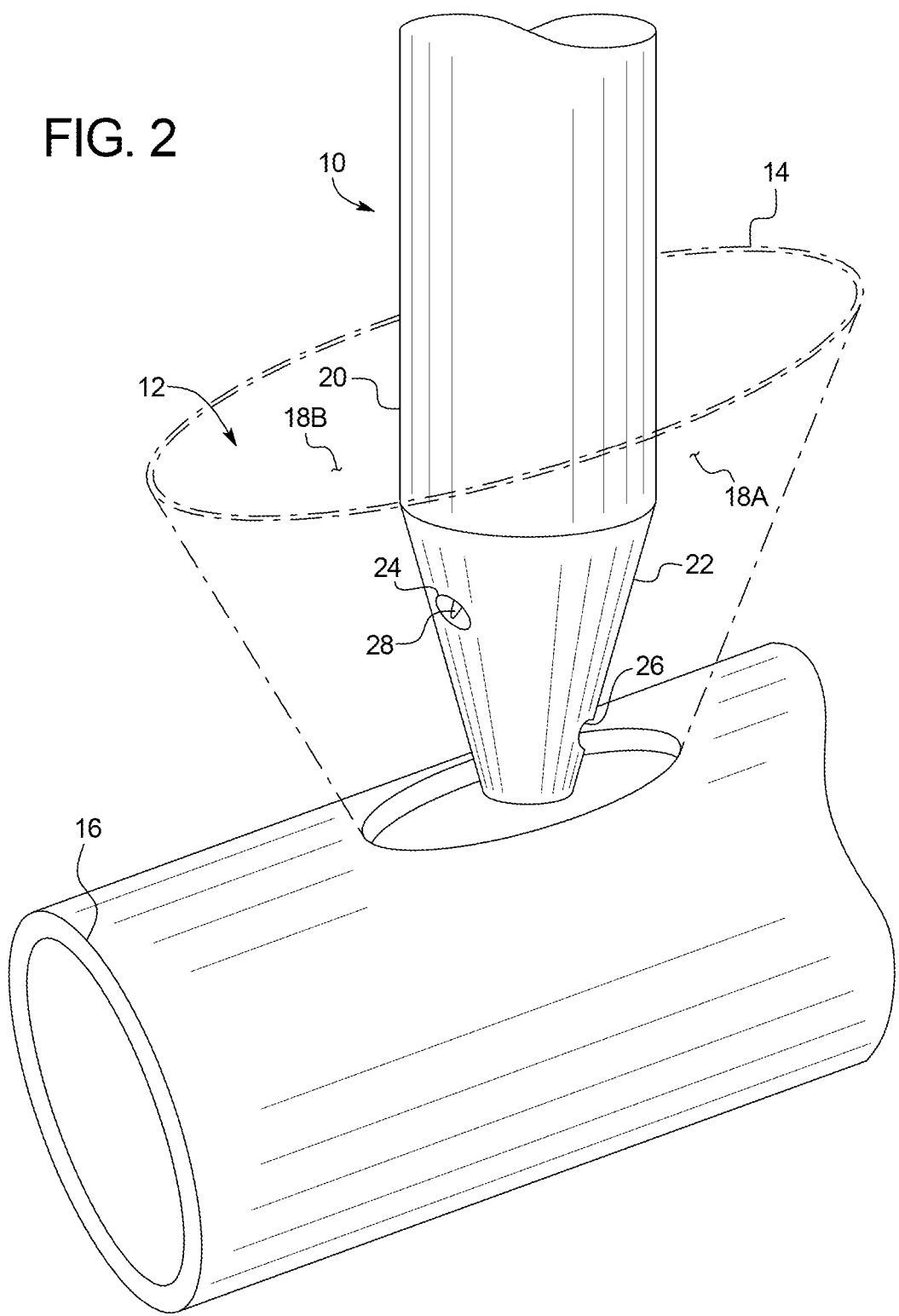
FIG. 2 is a plan view of the method of closing a wound, showing the wound closure device inserted into the wound.
Figure 3:
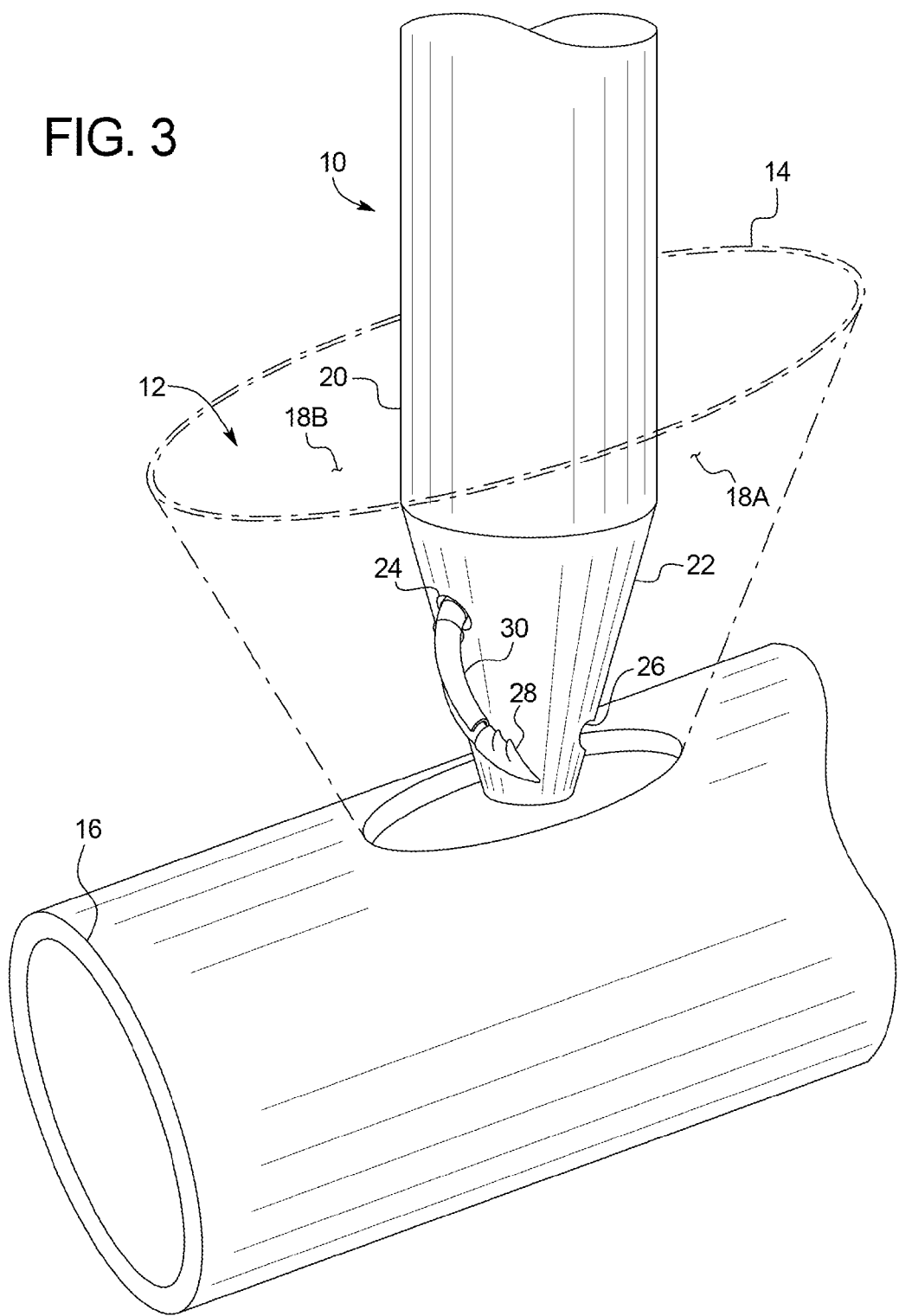
FIG. 3 is a plan view of the method of closing a wound, showing a pusher with a sharp tip penetrating body tissue.

In FIG. 2, the wound closure device 10 is shown inserted into the wound 12 before the closure device 10 is actuated. Prior to actuation, it is preferred that the sharp tip 28 remain fully within the first port 24 without being exposed during positioning of the housing 20 into the wound 12. In FIG. 3, a pusher 30 and the sharp tip 28 at the end of the pusher 30 is shown extending from the first port 24. At this stage, the sharp tip 28 and the pusher 30 will be penetrating through the wall 18A of the wound 12. As shown, for example, in FIGS. 27-29, the wound closure device 10 may be provided with two pushers 30 and sharp tips 28, which may be oriented on opposite sides of the housing 20. Thus, in FIG. 3, the housing 20 may have two first and second ports 24, 26, and the corresponding pusher 30 and sharp tip 28 may penetrate the opposite wall 18B of the wound.

Figure 4:
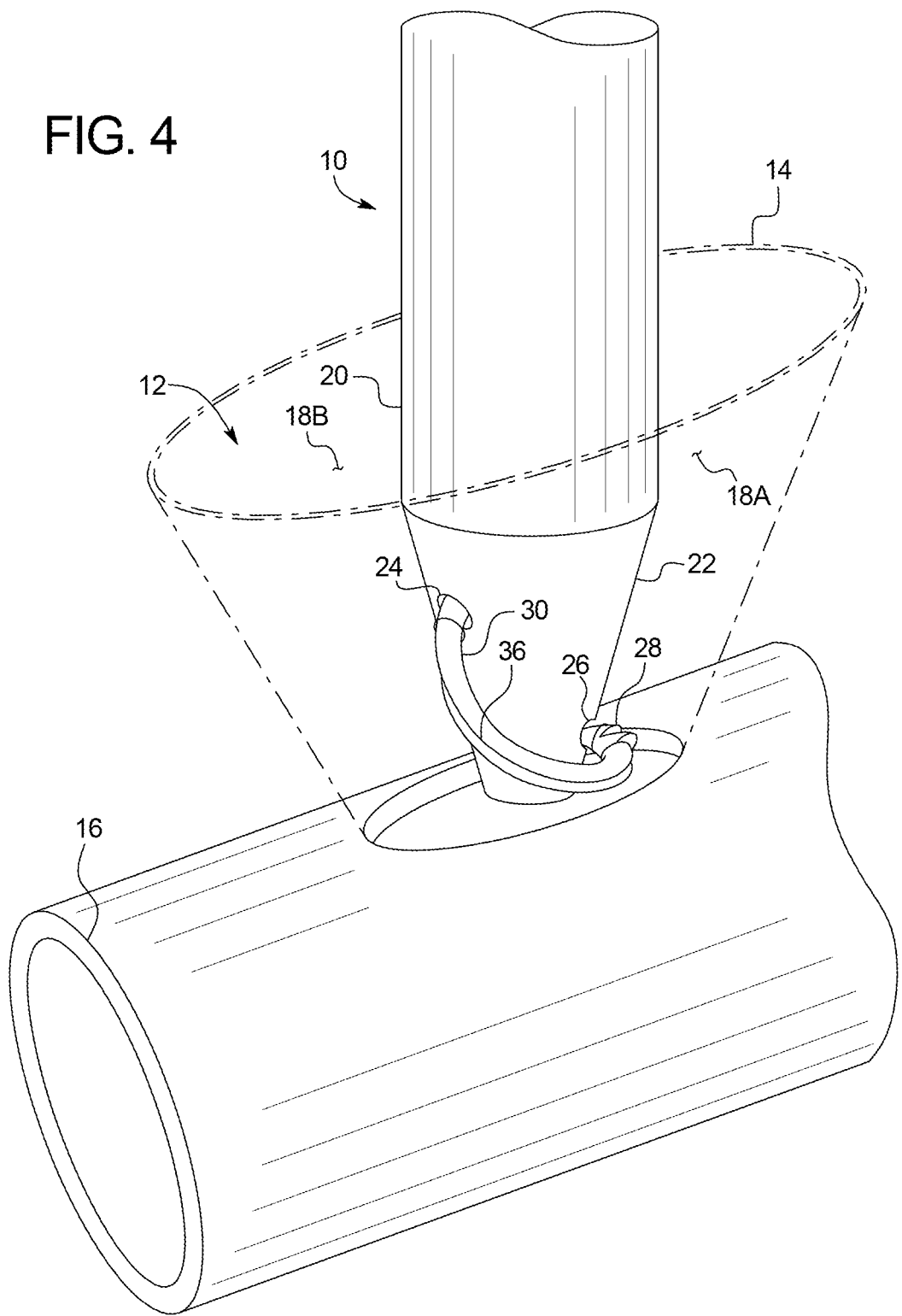
FIG. 4 is a plan view of the method of closing a wound, showing the pusher and sharp tip continuing to penetrate body tissue.
Figure 5:
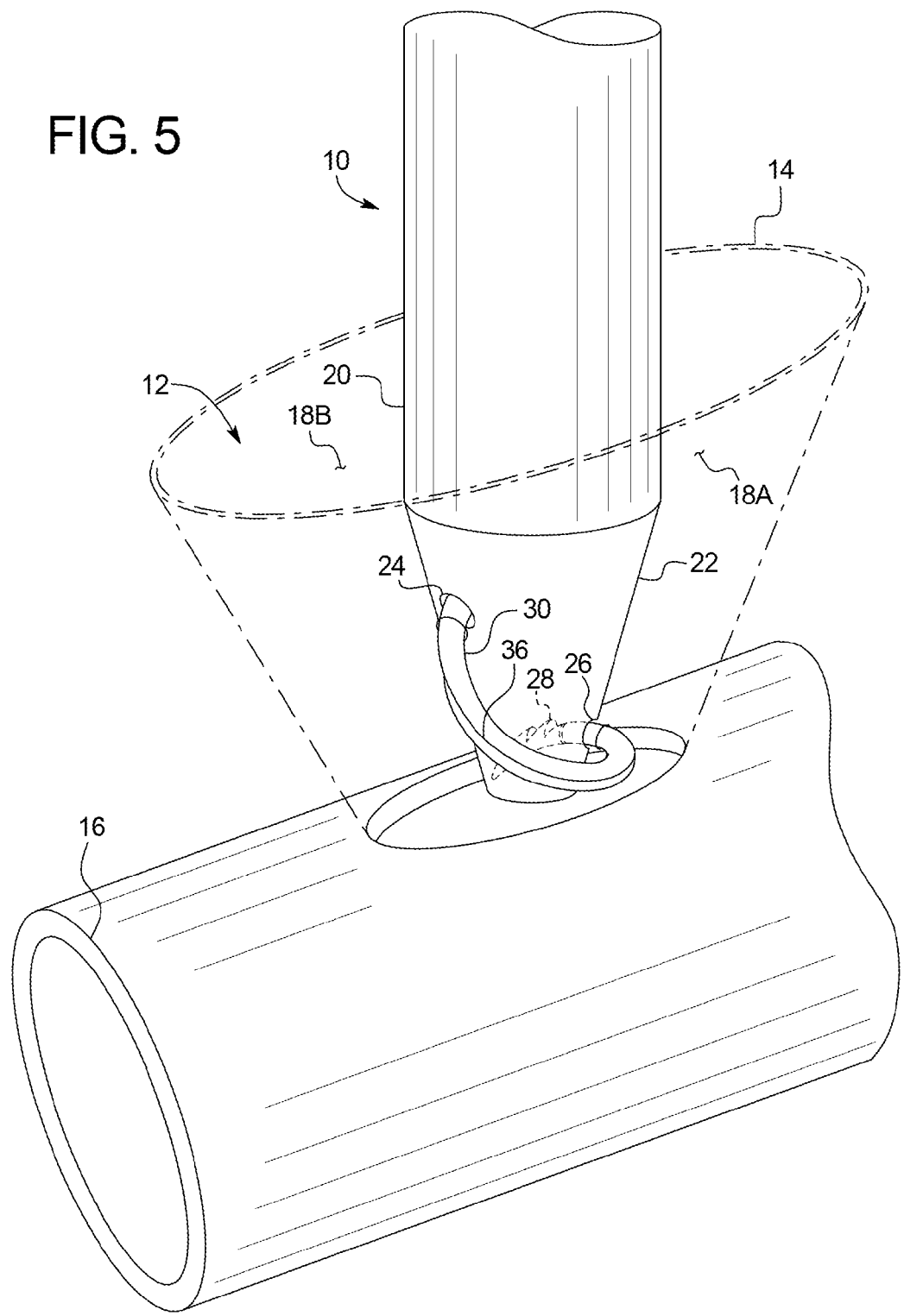
FIG. 5 is a plan view of the method of closing a wound, showing the pusher and sharp tip penetrating through the body tissue and being received by a second port in the housing of the wound closure device.

In FIG. 4, the sharp tip 28 and pusher 30 are shown completely or almost completely penetrating through the wall 18 of body tissue. As shown, the sharp tip 28 is shown starting to enter the second port 26. In FIG. 5, the sharp tip 28 is shown fully received by the second port 26.

Figure 6:
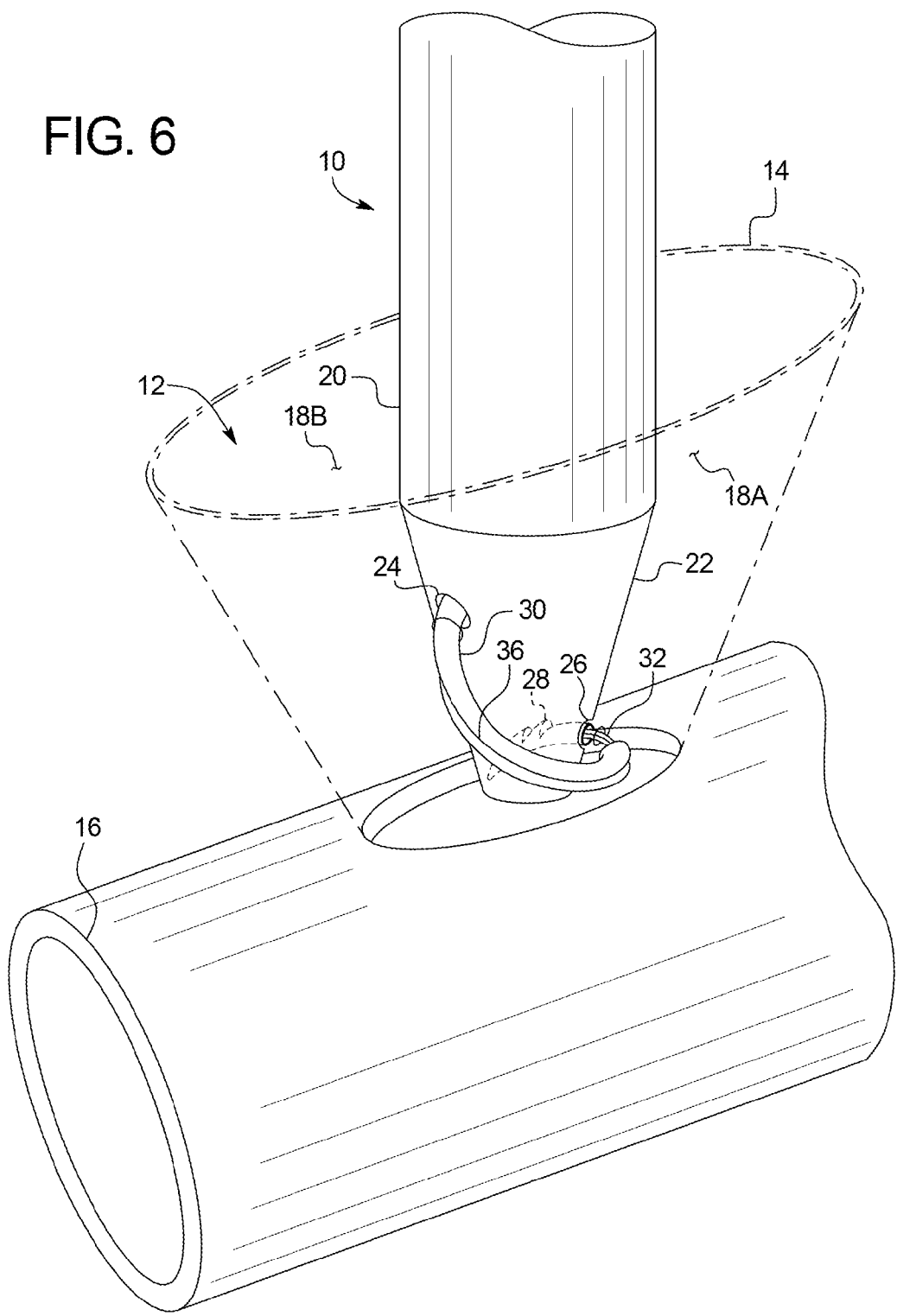
FIG. 6 is a plan view of the method of closing a wound, showing the pusher being retracted while the sharp tip remains in the second port.
Figure 7:
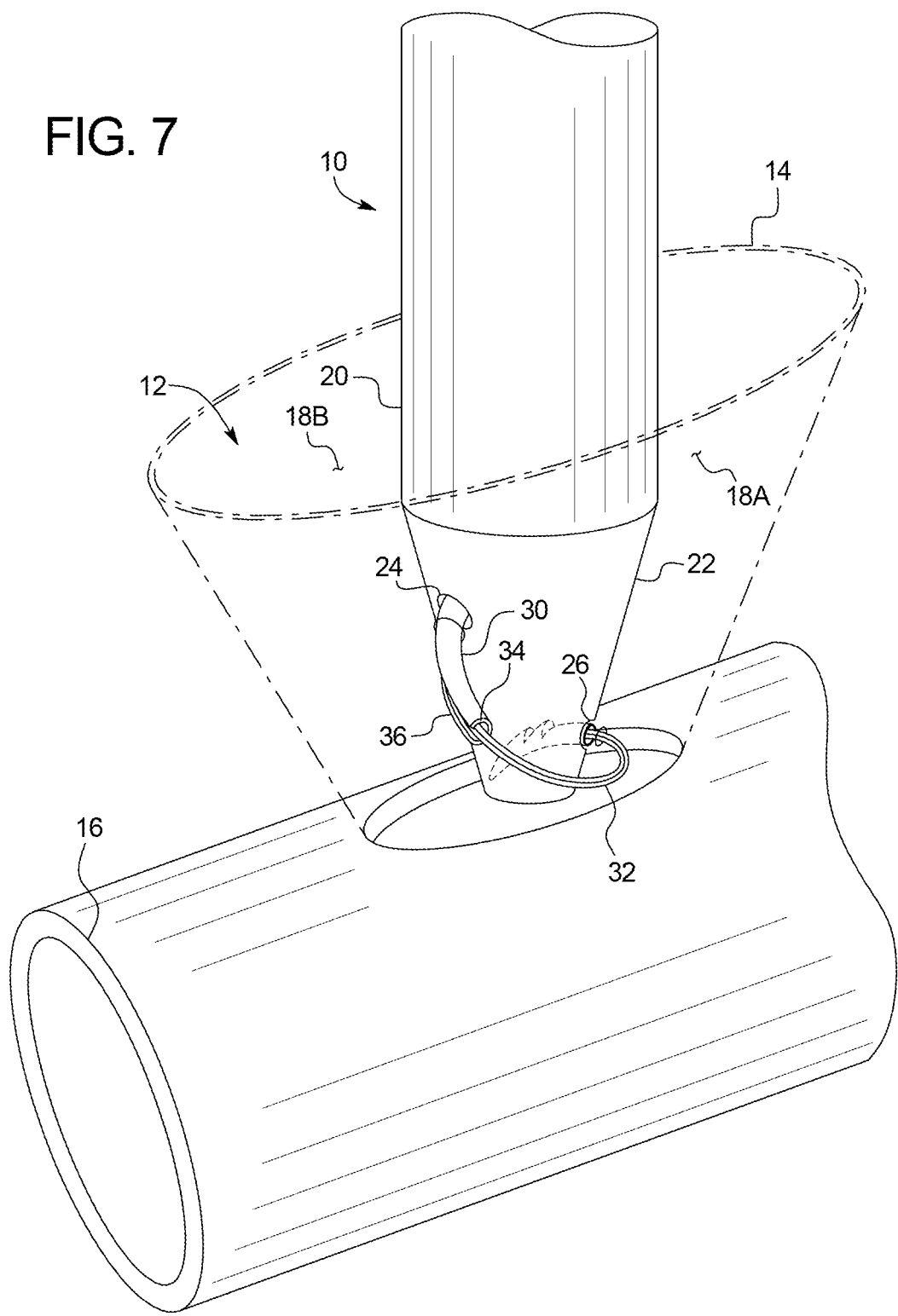
FIG. 7 is a plan view of the method of closing a wound, showing the pusher continuing to be retracted while the suture portion remains extending through the body tissue.

In FIG. 6, the pusher 30 is shown being retracted back through the wall 18 of body tissue and toward the first port 24. As shown, the sharp tip 28 may be separable from the pusher 30 and may remain in the second port 26 as the pusher 30 is retracted. A suture 32 may also be attached to the sharp tip 28, and thus, will remain extending through the body tissue wall 18 as the pusher 30 is retracted. In FIG. 7, the pusher 30 is shown retracted further back into the first port 24 while the suture 32 remains extending through the penetrated tissue wall 18. As shown, the pusher 30 may be hollow with a longitudinal cavity 34 through which the suture 32 may extend. Thus, as the pusher 30 is retracted, the suture 32 may extend out of the distal end of the longitudinal cavity 34. The pusher 30 may also have a longitudinal opening 36 along the outer edge of the cavity 34 so that the suture 32 may pass out of the longitudinal cavity 34 during retraction of the pusher 30. Alternatively, the suture 32 may extend through the longitudinal cavity 34 to an exit hole.

Figure 8:
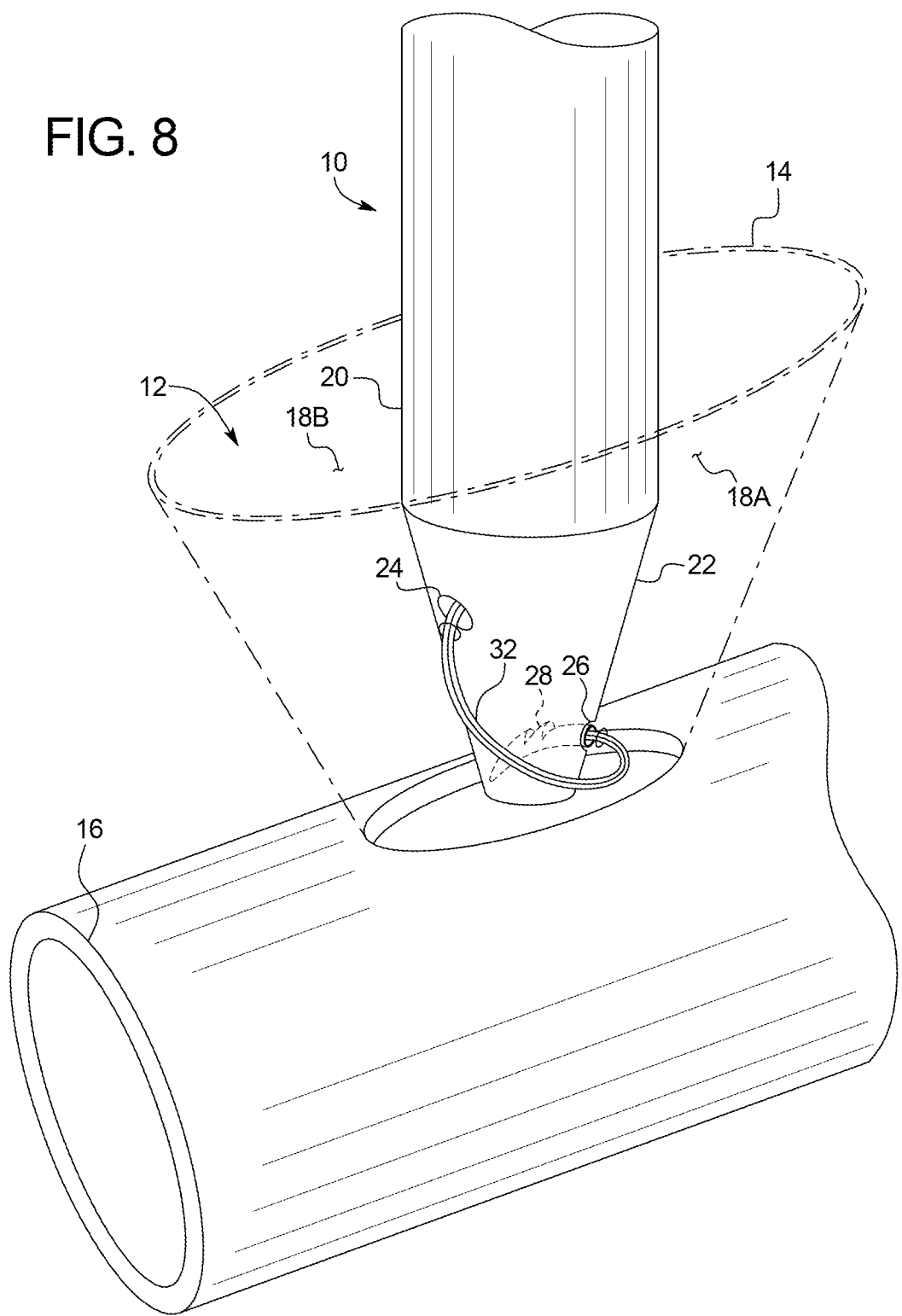
FIG. 8 is a plan view of the method of closing a wound, showing the pusher fully retracted.
Figure 9:
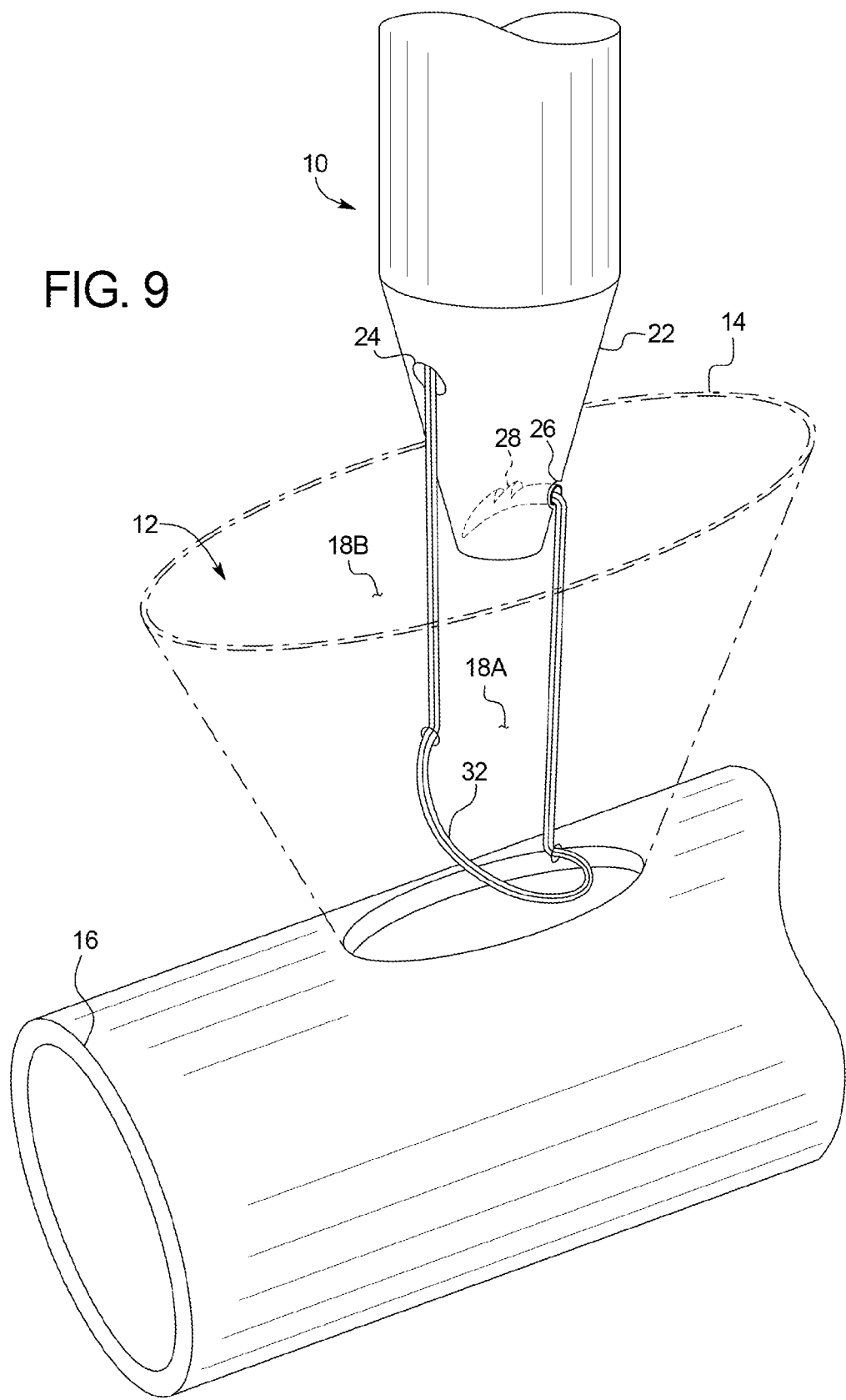
FIG. 9 is a plan view of the method of closing a wound, showing the wound closure device being withdrawn from the wound while the suture portion remains extending through the body tissue.

In FIG. 8, the pusher 30 is shown fully retracted into the housing 20 through the first port 24. In this particular embodiment, the suture 32 may extend through the first port 24, but in other embodiments, the suture 32 may extend out of the wound 12 outside of the housing 20. Preferably, the pusher 30 rotates about 180° to about 240° between the first and second ports 24, 26 as it is actuated and retracted. In FIG. 9, the housing 20 is shown being withdrawn from the wound 12. Since the sharp tip 28 and one end of the suture 32 remain retained at the second port 26, the suture 32 will feed out of the first port 24 and will thread through the penetrated tissue wall 18.

In FIG. 10, once sufficient suture 32 length has been threaded through the penetrated tissue wall 18, the suture 32 may be separated from the sharp tip 28 and the housing 20 by cutting the suture 32, etc. As shown, where two pushers 30 are used, the corresponding suture 32 may also be extending through the opposite tissue wall 18B. In this particular embodiment, the suture portions 32 are shown as two separate sutures 32, since each suture portion 32 initially extended through separate first ports 24, and thus, a complete separation of the two suture portions 32 would be needed to separate the suture portions 32 from the housing 20. However, in other embodiments, for example, where the suture 32 extends out of the wound 12 along the exterior of the housing 20, it may be possible for the suture portions 32 to be connected in the middle so that the two suture portions 32 are the ends of a single, long suture 32. Once the suture portions 32 have been fully threaded through the penetrated tissue walls 18A, B, the sutures 32 may be tightened to pull the tissue walls 18A, B together. The sutures 32 may then be secured together, for example, by knotting to complete the procedure.

Figure 12:
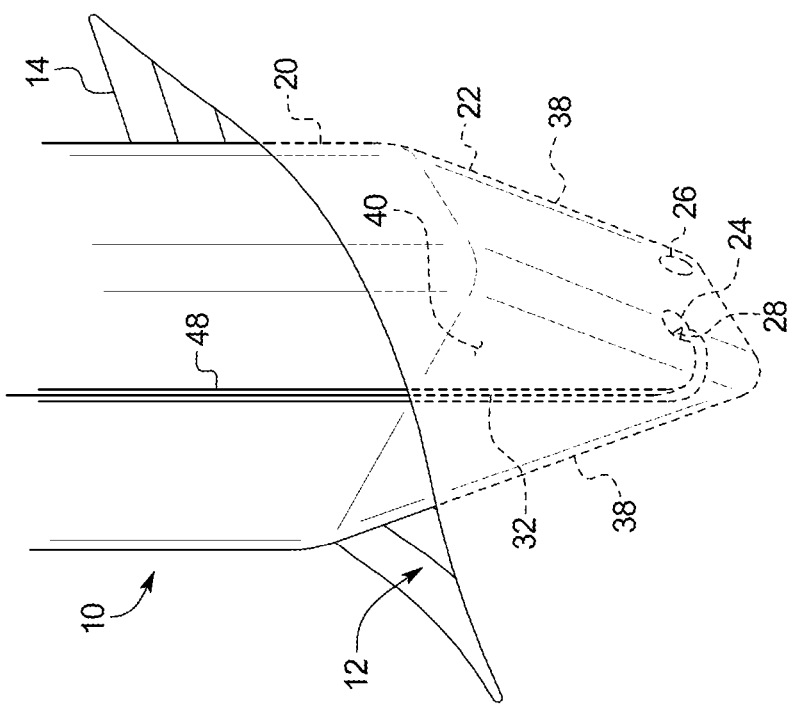
FIG. 12 is a plan view of the wound closure device, showing the wound closure device inserted into the wound.

Another embodiment of the wound closure device 10 is shown in FIGS. 11-25. As shown in FIG. 11, the housing 20 may have a tapered portion 22 with opposing tapered surfaces 38 and flat side surfaces 40. While the pusher 30 is positioned inside of the housing 20, the pusher 30 is shown in solid lines to better illustrate the pusher 30. As shown, at least the distal portion of the pusher 30 has a helical shape 42. If desired, the pusher 30 may have a drive joint 44 so that a vertical driveshaft 46 extends generally vertical while the helical portion 42 of the pusher 30 extends at an angle from the driveshaft 46. In this embodiment, the suture 32 may extend along the exterior of the housing 20 away from the sharp tip 28. If desired, a channel 48 may be provided along the exterior of the housing 20 for the suture 32 to extend within. In FIG. 12, the wound closure device 10 is shown inserted into the wound 12 before the pusher 30 is actuated.

FIGS. 13-16 show the pusher 30 prior to being actuated. As shown, it is preferable for the sharp tip 28 to be fully withdrawn into the housing 20 prior to actuation to avoid scraping the sharp tip 28 on the walls 18 of the wound 12 during insertion of the device 10. FIGS. 17-20 show the pusher 30 fully actuated through the first port 24. As shown, the sharp tip 28 is received by the second port 26. As shown most clearly in FIG. 19, the suture 32 extends from the exterior channel 48 along the housing 20 and through the longitudinal cavity 34 in the pusher 30. FIGS. 21-22 also show the pusher 30 and sharp tip 28 prior to actuation, and FIGS. 23-24 also show the pusher 30 and sharp tip 28 fully actuated. FIGS. 25-26 show the pusher 30 retracted after being actuated. As shown, the sharp tip 28 remains in the second port 26, and the suture 32 extends from the second port 26 along the helical path that the pusher 30 followed during actuation.

Another embodiment of the wound closure device 10 is shown in FIGS. 27-28. In FIG. 27, the sharp tips 28 of two pushers 30 are shown received within respective second ports 26. As shown, the second ports 26 may be generally aligned circumferentially but may be longitudinally offset. FIG. 28 shows the pushers 30 extending from the first ports 24. Like the second ports 26, the first ports 24 may be generally circumferentially aligned and longitudinally offset from each other.

Figure 29:
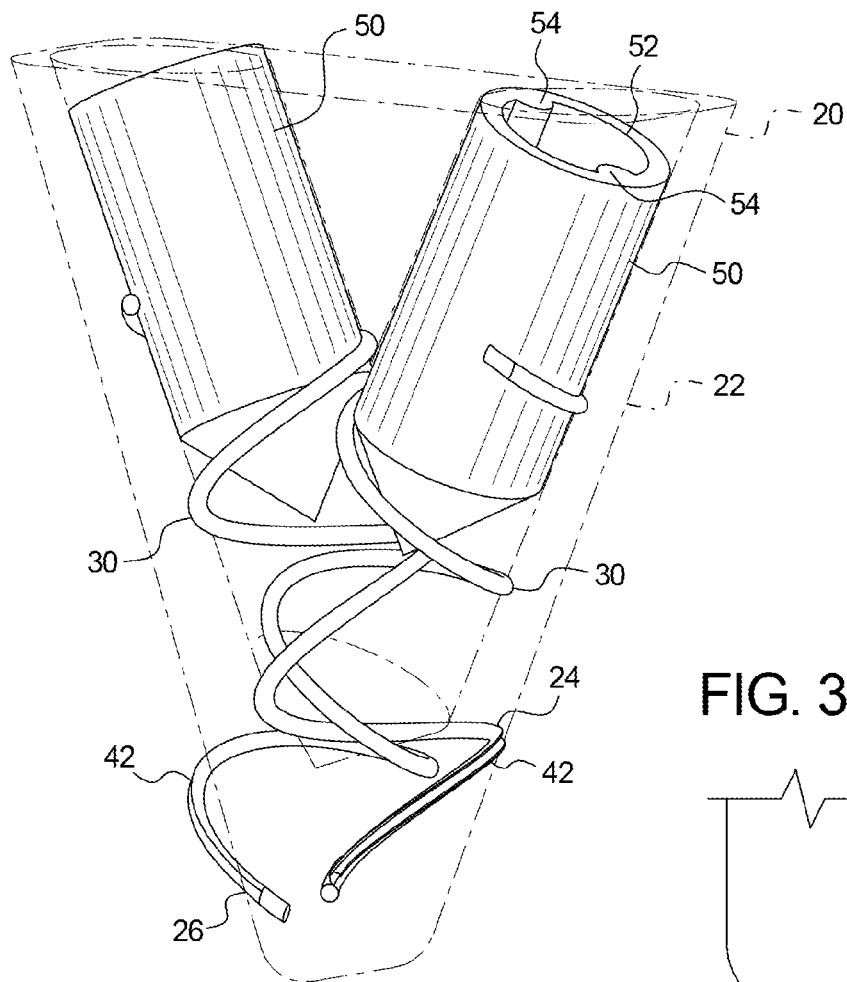
FIG. 29 is a perspective view of another embodiment of a wound closure device, showing the pusher members actuated.
Figure 35:
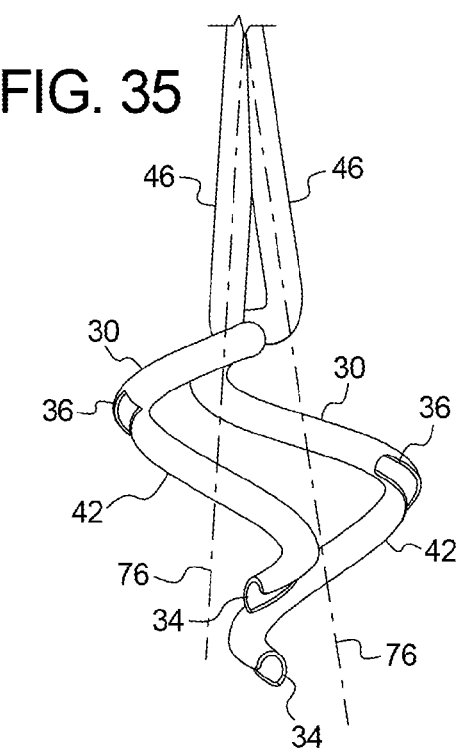
FIG. 35 is a perspective view of two pushers in a retracted state.

Another embodiment of the wound closure device 10 is shown in FIG. 29. In order to better illustrate the device 10, the pushers 30 are shown with solid lines although most of the structure is located within the housing 20. As shown, the pushers 30 have a helical shape 42 along the distal portion. Thus, the pushers 30 and sharp tips 28 follow a helical path as they are actuated. In FIG. 29, the pushers 30 are provided with a drive portion 50 having a socket 52 for a driveshaft 46. However, as shown in FIG. 35, the drive joint 44 may be omitted if desired. In order to actuate the pushers 30, the pushers 30 are rotated in opposite directions with respect to each other. Preferably, the helical paths of the pushers 30 extend along at least a portion of the tapered portion 22. For example, the first and second ports 24, 26 may both be located along the tapered portion 22. As shown, the helical portions 42 of the pushers 30 may be angled relative to each other so that they are angled toward each other toward their distal ends. However, the helical portions 42 may also be angled outward away from each other toward their distal ends as shown in FIG. 35. In order to reduce the profile of the closure device 10, it may be desirable for the helical paths of the pushers 30 to circumferentially overlap each other within the housing 20.

Figure 30:
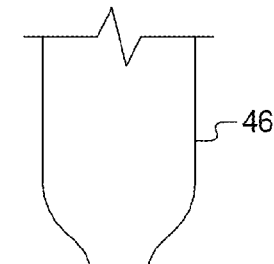
FIG. 30 is a perspective view of a drive mechanism for the wound closure device.
Figure 31:
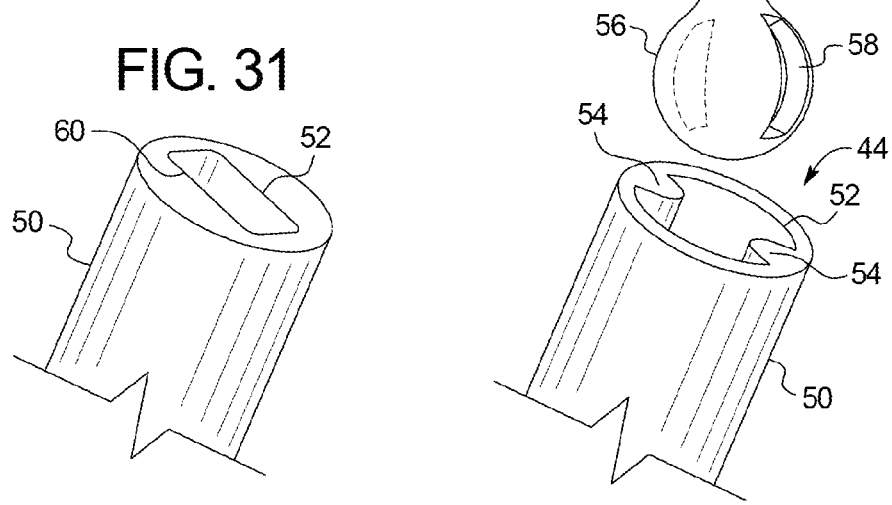
FIG. 31 is a perspective view of another drive receiver for the wound closure device.
Figure 32:
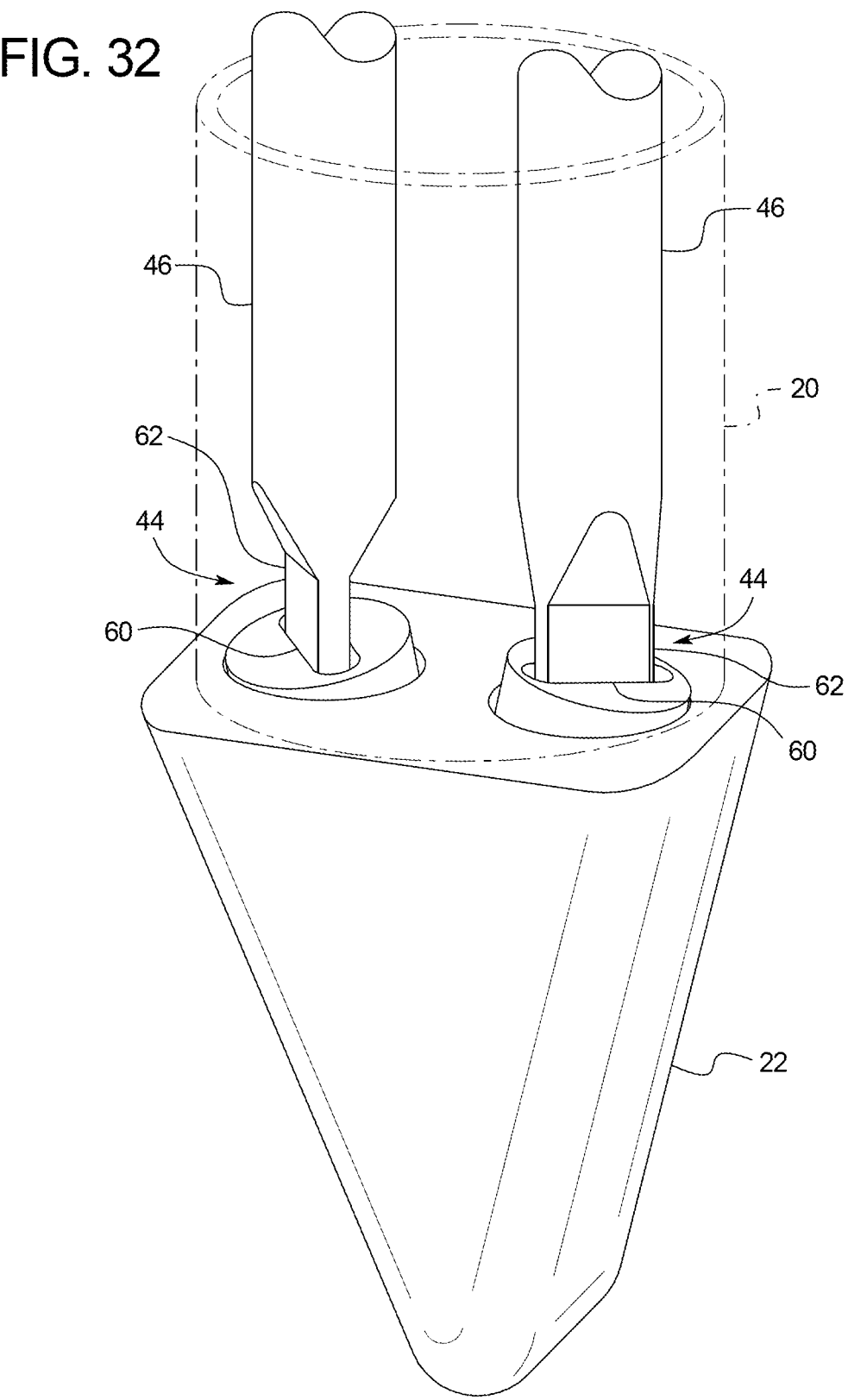
FIG. 32 is a perspective view of another drive mechanism for the wound closure device.

FIG. 30 shows one embodiment of a drive joint 44. Like FIG. 29, the pusher 30 is provided with a socket 52 and internal half-round drive ribs 54. The driveshaft 46 may be provided with a round drive end 56 with corresponding drive recesses 58 receiving the ribs 54 or the recesses 58 could be outward extending ribs. FIG. 31 shows another pusher 30 with a rectangular drive slot 60. FIG. 32 shows drive joints 44 with a generally rectangular drive slots 60 in the pushers 30 and corresponding generally rectangular drive ends 62 on the driveshafts 46. As shown, the driveshafts 46 may be generally parallel to each other.

Figure 33:
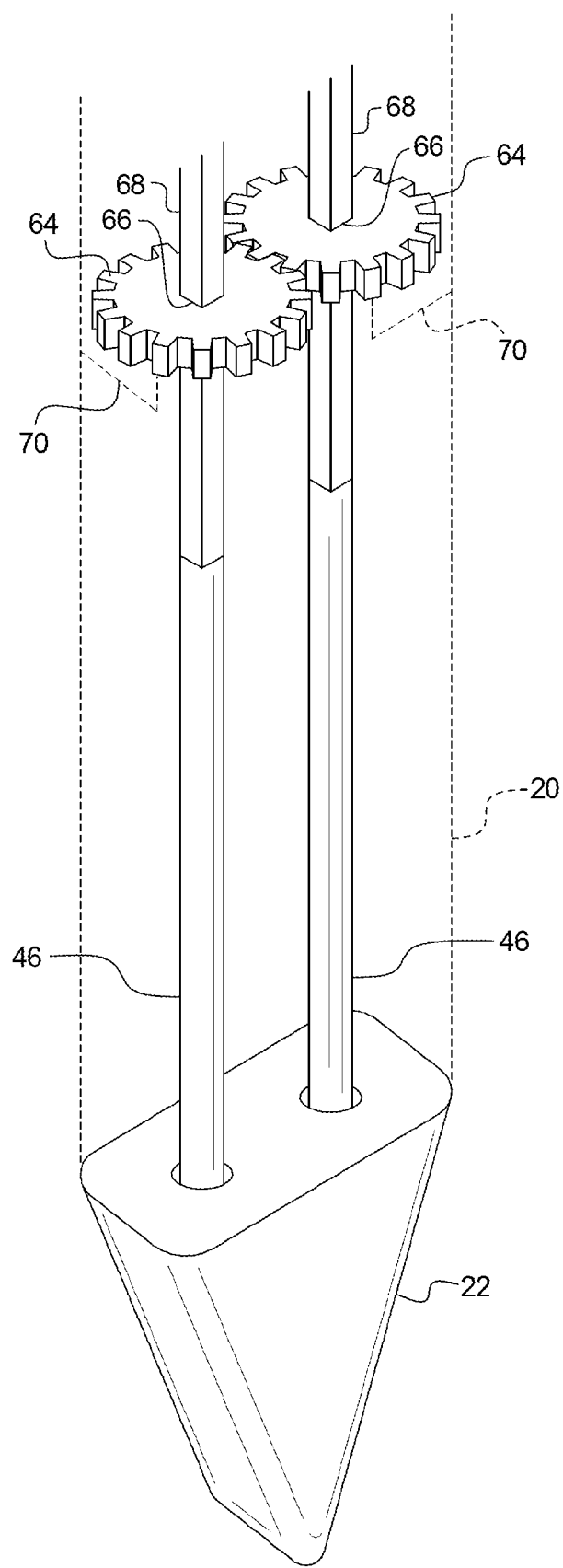
FIG. 33 is a perspective view of another drive mechanism for the wound closure device.
Figure 34:
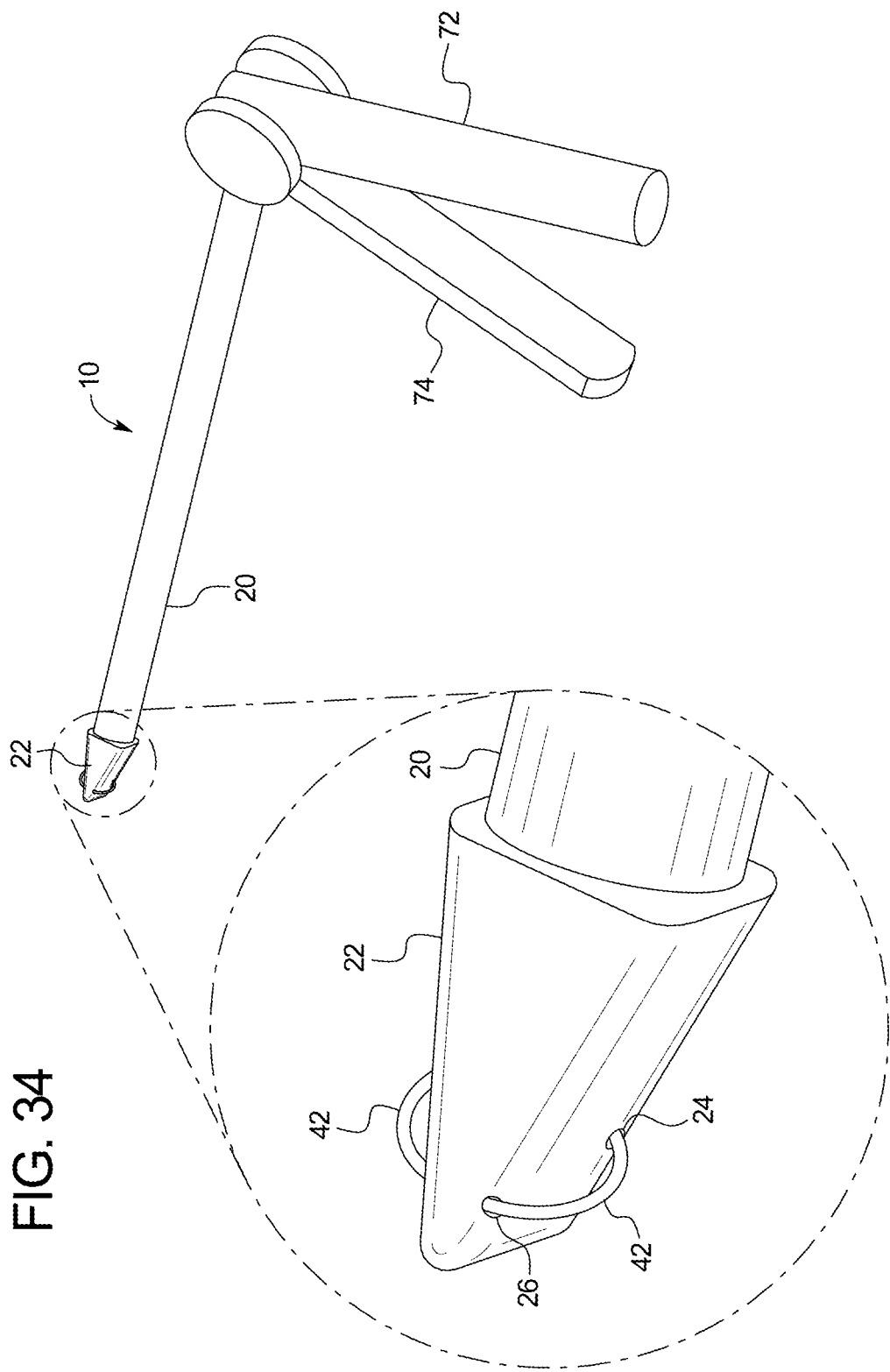
FIG. 34 is a perspective view of another drive mechanism for the wound closure device.

In FIG. 33, a geared drive mechanism 64 is shown. As shown, the driveshaft 46 for both pushers 30 may be geared 64 together so that rotation of one driveshaft 46 causes an equal amount of rotation in the other driveshaft 46. As noted above, the geared arrangement 64 between the pushers 30 will cause the pushers 30 to rotate in opposite directions relative to each other. The gears 64 may be engaged with the driveshafts 46 to permit the driveshafts 46 to slide relative to the gears 64 as the driveshafts 46 rotate and move longitudinally. For example, the driveshafts 46 and corresponding bores 66 of the gears 64 may be non-round 68, such as square, splined, etc. The gears 64 may also be supported by support walls 70 in the housing 20 to prevent the gears 64 from moving longitudinally as the pushers 30 are rotated. Alternatively, the gears 64 could be fixed to the driveshafts 46, and the drive gears 64 could be permitted to move longitudinally with the driveshafts 46 during rotation if desired. Although the pushers 30 may be driven in a number of different ways, FIG. 34 shows a handle 72 with a lever 74 mechanism that may be used by a physician to actuate the pushers 30.

Figure 36:
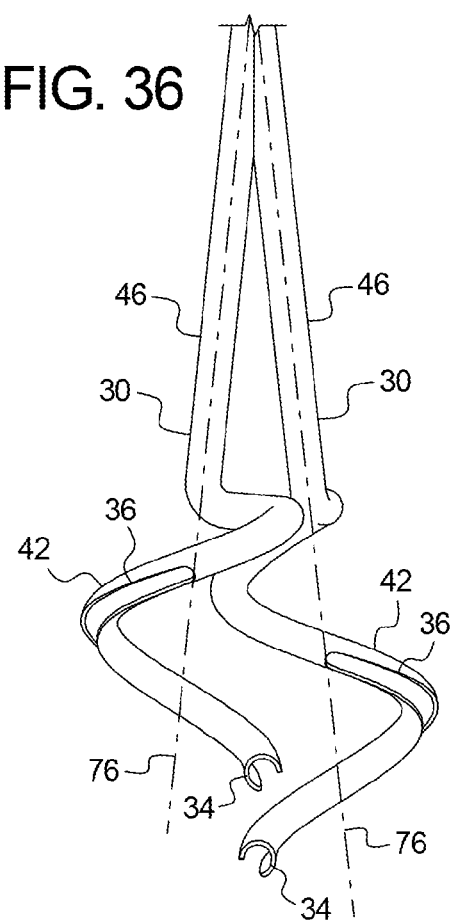
FIG. 36 is a perspective view of the two pushers in an extended state.
Figure 37:
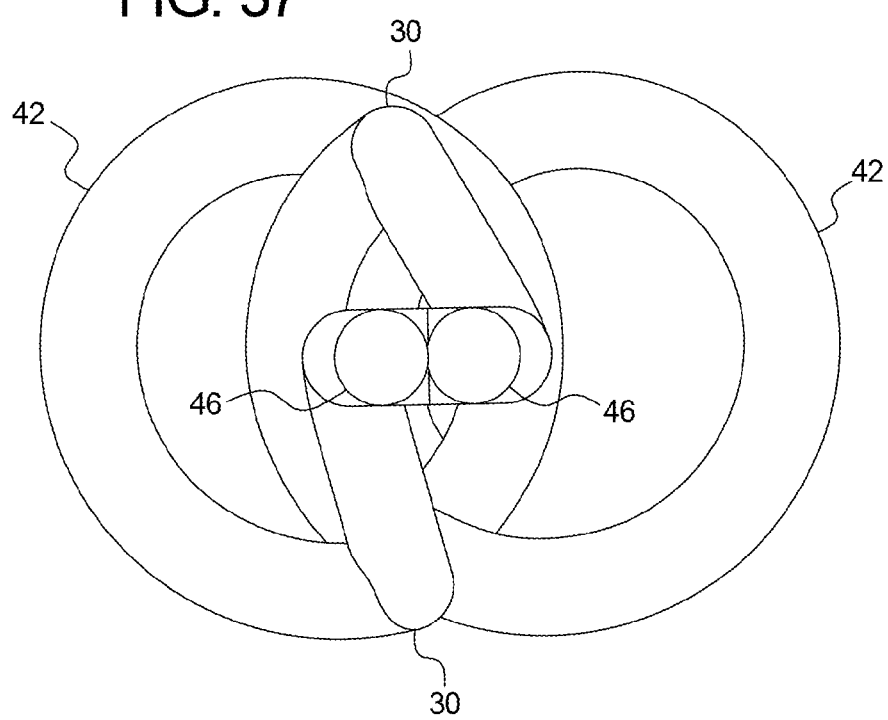
FIG. 37 is a top view of the two pushers in the retracted state.

FIGS. 35-37 show the pushers 30 by themselves to better illustrate the pushers 30. In FIG. 35, the pushers 30 are shown in the initial, retracted position. In FIG. 36, the pushers 30 are shown in the extended, actuated position. As shown, the helical distal portion 42 of the pushers 30 may be hollow with a longitudinal cavity 34 and longitudinal opening 36 to the cavity 34 along the outer edge. In this embodiment, the drive joint 44 may be omitted and the driveshaft 46 may be directly connected to the helical portion 42 of each pusher 30. Preferably, the driveshaft 46 is solid, i.e., non-hollow, and is connected to the hollow helical portion 42 with solder or welding. The driveshafts 46 may also be connected to the helical portions 42 along the centerline of the helical portions 42. As shown in FIG. 37, the helical paths of the helical portions 42 may circumferentially overlap. This enables the profile of the closure device 10 to be reduced in size. Because the helical portions 42 overlap in this particular embodiment, the helical paths may be longitudinally offset from each other. As described above, the first ports 24 and the second ports 26 may also be longitudinally offset. It may also be desirable for one of the helical portions 42 to be longer than the other helical portion 42 to accommodate the longitudinal offset. For example, in FIGS. 35-36, the right helical portion 42 may be longer than the left helical portion 42 so that the proximal ends are generally longitudinally aligned but the distal ends are longitudinally offset. For example, the left helical portion 42 may have about 1¼ turns along the helical path, while the right helical portion 42 may have about 1½ turns along the helical path.

As shown in FIGS. 35-36, the helical shape 42 of the distal portion of each of the pushers 30 may be defined by a central axis 76 around which the helical path extends. In this embodiment, the helical portions 42, and thus the axes 76, may be angled outward toward the distal ends with respect to each other. Preferably, the included angle between the axes 76 is about 8° to about 16°, and most preferably about 12°. As shown in FIGS. 35-37, because the drive shafts 46 extend generally along the axes 76 of the helical portions 42 and are angled toward each other, the drive shafts 46 may intersect each other proximally from the helical portions 42. However, in practice this intersection may be avoided by using drive shafts 46 that are moderately flexible so that the drive shafts 46 bend away from the axes 76 of the helical portions 42 and away from the potential intersection. The drive shafts 46 may then extend generally vertical towards the handle. Alternatively, unlike FIG. 37 where the pushers 30 are located on the same transverse plane, the pushers 30 could be laterally offset to prevent interference between the drive shafts 46.

Figure 38:
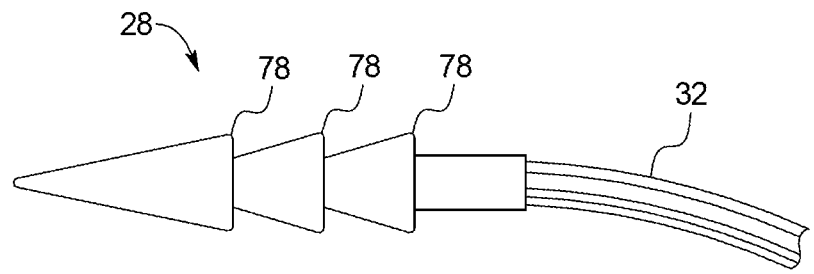
FIG. 38 is a side view of a sharp tip with a suture attached to the sharp tip.
Figure 39:
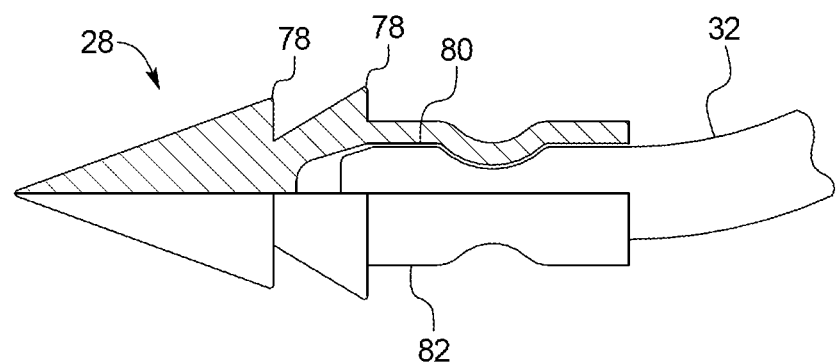
FIG. 39 is a sectional view of a sharp tip with a suture attached to the sharp tip.

In FIGS. 38-39, the sharp tip 28 is shown with an end of the suture 32 attached to the sharp tip 28. In FIG. 38, the sharp tip 28 is shown with three circumferential edges 78, while in FIG. 39, the sharp tip 28 is shown with two circumferential edges 78. As explained further below, the circumferential edges 78 may act as catches 78. In FIG. 39, the end of the suture 32 is shown swaged within a proximal lumen 80 of the sharp tip 28. Alternatively, the suture 32 may be bonded, knotted or melted to secure the suture 32 and sharp tip 28 together.

Figure 40:
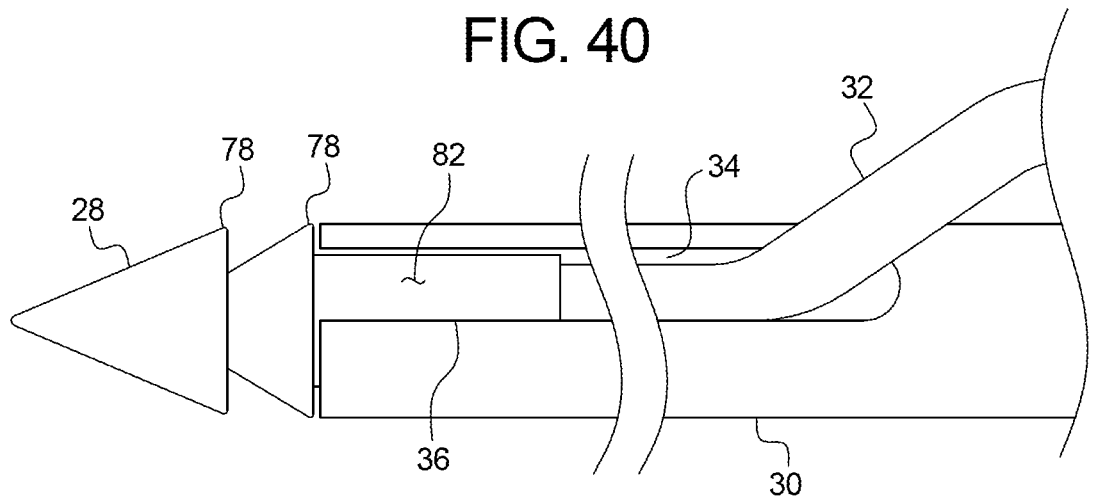
FIG. 40 is a side view of the sharp tip engaged with the end of the pusher.
Figure 41:
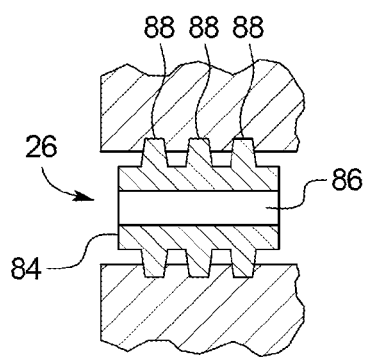
FIG. 41 is a sectional view of a catch within the housing.

In FIG. 40, the sharp tip 28 is shown engaged with the distal end of the pusher 30. Preferably, the sharp tip 28 has a shaft portion 82 that slides into the longitudinal cavity 34 of the pusher 30. The diameter of the shaft portion 82 is also preferably larger than the width of the longitudinal opening 36. Thus, the sharp tip 28 is laterally restrained within the longitudinal cavity 34 and is unable to laterally slip out of the longitudinal opening 36. The diameter of the circumferential edges 78 is also preferably generally the same as the outer diameter of the distal end of the pusher 30. As shown in FIG. 40, the most-proximal circumferential edge 78 may abut the distal end of the pusher 30 and may serve as an engagement ledge 78 for the pusher 30 to push against. As described further below, the distal circumferential edge 78 may serve as a catch 78. As also shown in FIG. 40, the suture 32 extends along a length through the longitudinal cavity 34 and passes out of the longitudinal cavity 34 through the longitudinal opening 36.

Figure 42:
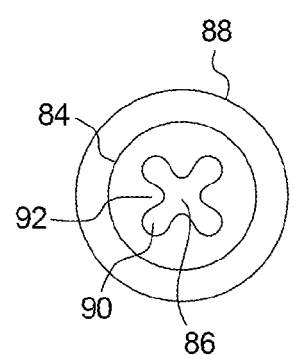
FIG. 42 is a front view of another catch.
Figure 43:
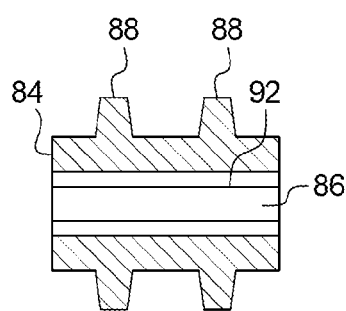
FIG. 43 is a sectional view of the catch of FIG. 42.
Figure 44:
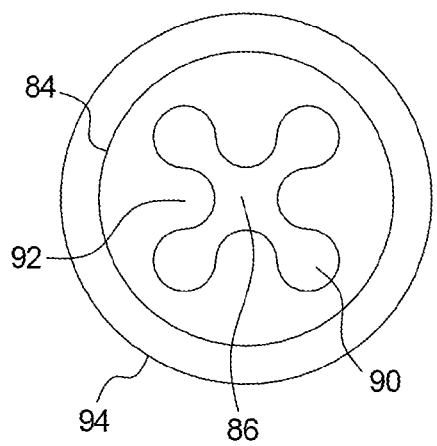
FIG. 44 is a front view of another catch.
Figure 45:
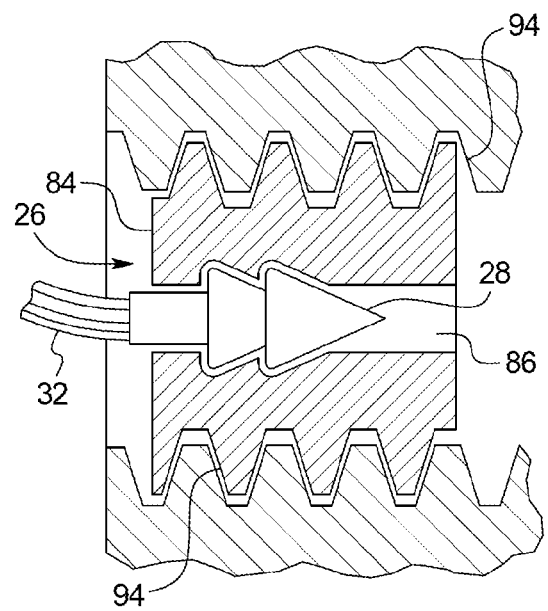
FIG. 45 is a sectional view of the catch of FIG. 44 within the housing.
Figure 46:
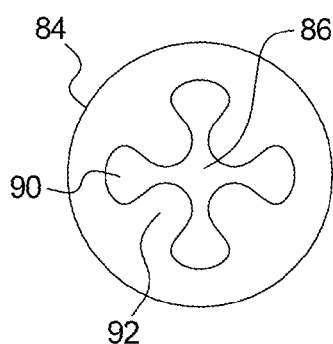
FIG. 46 is a front view of another catch.
Figure 47:
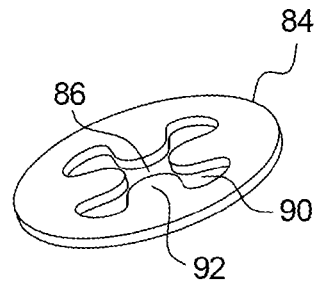
FIG. 47 is a perspective view of the catch of FIG. 46.
Figure 48:
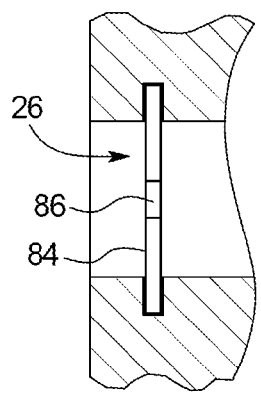
FIG. 48 is a sectional view of the catch of FIG. 46 within the housing.
Figure 49:
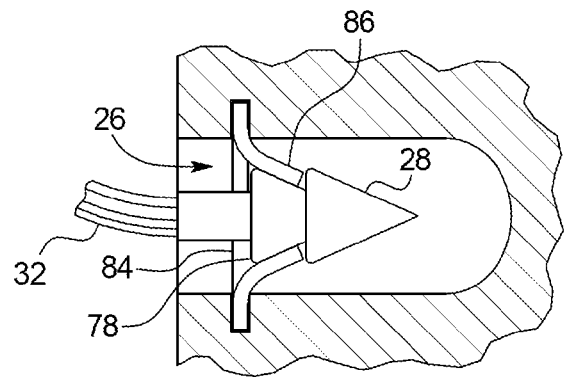
FIG. 49 is a sectional view of the catch of FIG. 46 receiving a catch on the sharp tip.
Figure 50:
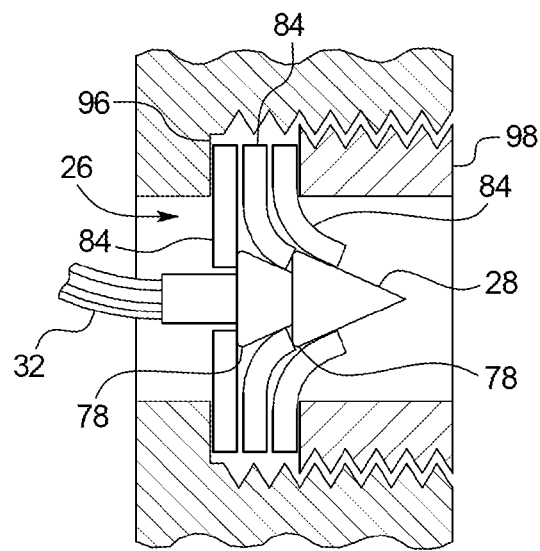
FIG. 50 is a sectional view of another catch within the housing receiving catches on the sharp tip.

As shown in FIGS. 41-50, a catch 84 may be located in the second port 26 to retain the sharp tip 28 when the sharp tip 28 is pushed into the second port 26. Preferably, the catch 84 in the second port 26 is made of a soft, elastic material like silicone, rubber or a soft plastic that deflects around the sharp tip 28 and may catch against a circumferential edge 78, or catch 78, on the sharp tip 28. For example, in FIG. 41, the second port catch 84 may be a soft elastomer with an axial opening 86. On the outer surface, the catch 84 may be provided with circumferential ribs 88 to fix the catch 84 inside of the second port 26. The ribs 88 may fix the catch 84 in the port 26 merely by deflecting the ribs 88, or adhesive may be applied to the outer surface of the catch 84 and the ribs 88. As shown in FIGS. 42-43, the axial opening 86 of the catch 84 may have channels 90 and ribs 92 instead of being circular like in FIG. 41. In FIGS. 44-45, the outer surface of the catch 84 and the inner diameter of the second port 26 may have corresponding threads 94 to fix the catch 84 in the port 26. FIG. 45 also shows how the axial opening 86 of the catch 84 deforms around the sharp tip 28 to wrap around and retain the catches 78 on the sharp tip 28. FIGS. 46-49 show the second port catch 84 as a thin disk 84 with an axial opening 86 with channels 90 and ribs 92. The thickness of the thin disk 84 may be less than the length between adjacent circumferential edges 78 on the sharp tip 28. As shown in FIG. 49, this embodiment of the second port catch 84 may be easier to push the sharp tip 28 through and may more securely engage the catch 78 on the sharp tip 28. As shown in FIG. 50, multiple thin disks 84 may also be used for the second port catch 84. For example, three thin disks 84 may be used for the catch 84. As also shown, the catch 84 may be secured into the housing 20 with a counterbore 96 and a threaded retainer 98. Other types of retention systems may also be possible for retaining the sharp tip 28 and suture 32 at the second port 26. For example, an active retainer that grasps or anchors the sharp tip 28 may be used. Alternatively, a system that pulls the sharp tip 28 and/or suture 32 through at least a portion of the housing 20 may be used.

Figure 51:
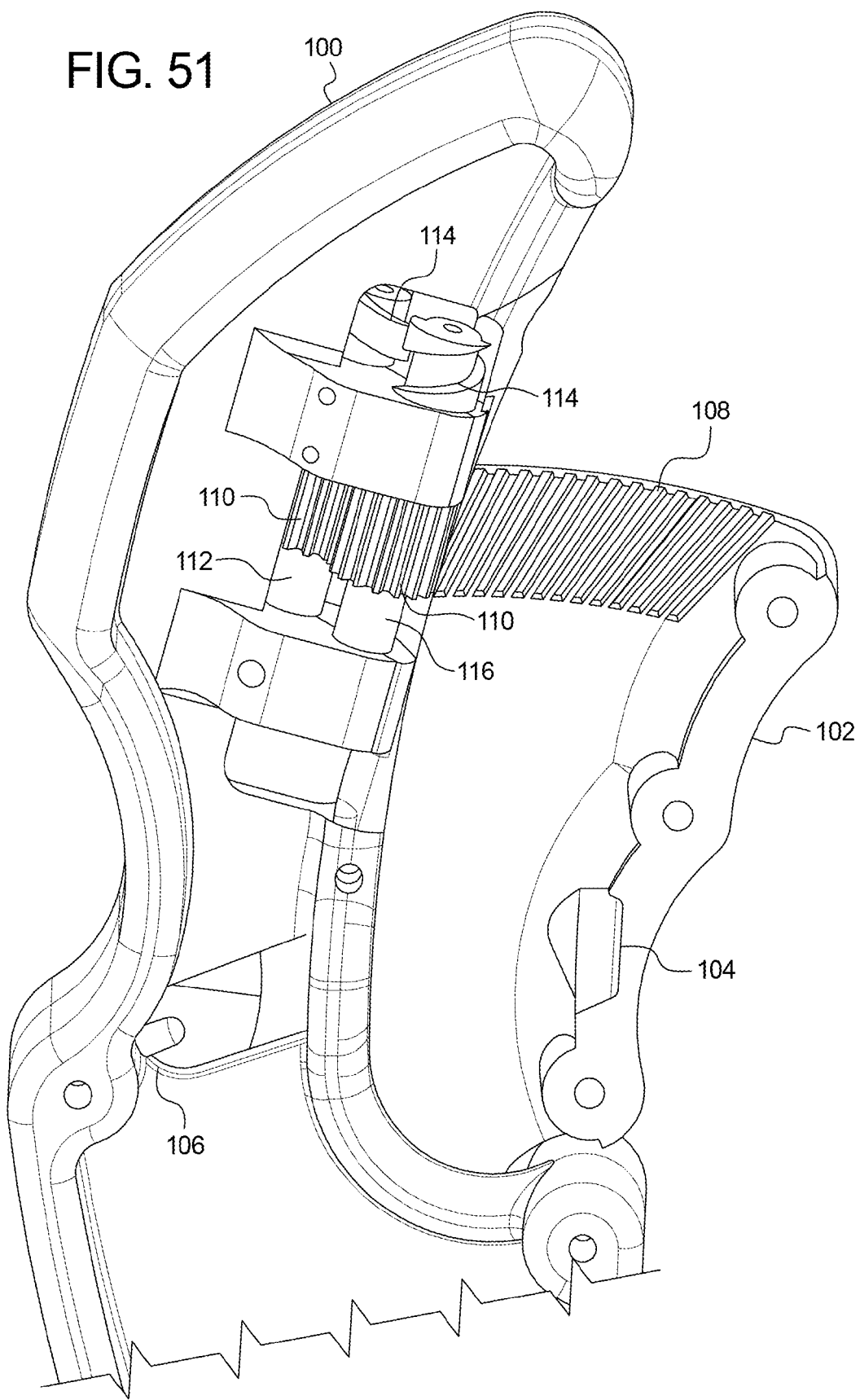
FIG. 51 is a perspective view of a handle to rotate and advance and retract the pushers.

A handle 100 is shown in FIG. 51 that may be used to rotate the pushers 30 while advancing and retracting the pushers 30. The handle 100 includes a lever 102 that is movable relative to the handle 100. For example, the lever 102 may be pivotally attached to the handle 100. A spring (not illustrated for simplicity) may be provided between a lever spring seat 104 and a handle spring seat 106 to bias the lever 102 away from the handle 100. The lever 102 includes a rack 108 of gear teeth that engages the teeth 110 of a first pinion 112 which is mounted within the handle 100 to allow rotation of the first pinion 112. The first pinion 112 is also provided with a helical thread 114 that is threadably engaged with a non-moving portion of the handle 100. Thus, when the lever 102 is pressed and moved toward the handle 100, the first pinion 112 rotates due to the engagement of the teeth 110 between the rack 108 and the pinion 112. At the same time, the first pinion 112 advances axially due to the threaded engagement 114 between the first pinion 112 and the housing 100. A second pinion 116 of similar design may also be engaged with the teeth 110 of the first pinion 112. Thus, when the first pinion 112 rotates, the second pinion 116 also rotates but in the opposite direction. Like the first pinion 112, the second pinion 116 may have a helical thread 114 engaged with the housing 100 so that the second pinion 116 axially advances as it rotates.

Although not illustrated in FIG. 51, the first and second pinions 112, 116 may each be connected to a drive shaft 46 to drive the pushers 30. When it is desired to reverse the direction of the pushers 30, the user releases the lever 102, which causes the spring to push the lever 102 back away from the handle 100. This causes the pinions 112, 116 to rotate in the reverse direction and retract axially back. The lengths of the pinion teeth 110 and the rack 108 are preferably sized to allow the desired axial advancement and retraction of the opinions 112, 116 during rotation. For example, the pushers 30 will typically need to be advanced and retracted about 3 mm to about 12 mm in use. If desired, the lever 102 may be provided with a matching, mirrored half that is attached to the lever 102 shown in FIG. 51. In this case, the first and second halves of the lever 102 would enclose the first and second opinions 112, 116. Also, the rack 108 of the first half would engage the teeth 110 of the first pinion 112 and the rack 108 of the second half would engage the teeth 110 of the second pinion 116. Since the racks 108 would be on opposite sides of the handle 100, the first and second pinions 112, 116 would rotate in opposite directions. Although the first and second pinions 112, 116 would not need to be engaged with each other where two separate racks 108 are provided, engagement between the pinion teeth 110 could be maintained to ensure reliable functioning of the handle 100.

While preferred embodiments of the invention have been described, it should be understood that the invention is not so limited, and modifications may be made without departing from the invention. The scope of the invention is defined by the appended claims, and all devices that come within the meaning of the claims, either literally or by equivalence, are intended to be embraced therein. Furthermore, the advantages described above are not necessarily the only advantages of the invention, and it is not necessarily expected that all of the described advantages will be achieved with every embodiment of the invention.

The invention claimed is:

1. A wound closure device, comprising:
   a first pusher comprising a distal portion with a helical shape;
   a housing supporting the first pusher, the distal portion of the first pusher being extendable along a helical path exterior from said housing;
   a first sharp tip disposed at a distal end of the distal portion of the first pusher; and
   a first suture portion engaged with the first pusher;
   wherein the first pusher is configured to push the first sharp tip along said helical path to penetrate body tissue, the first suture thereby being pulled through said body tissue along said helical path, the first suture thereafter being separable from the first pusher, and the first pusher being retractable from said body tissue along said helical path to leave the first suture extending through said body tissue,
   wherein said housing comprises a first port, the first sharp tip being disposed within said housing before penetrating said body tissue, and the first sharp tip and said distal portion of the first pusher configured to move outward through said first port to penetrate said body tissue,
   the wound closure device further comprising a second pusher comprising a distal portion with a helical shape, a second sharp tip disposed at a distal end of said distal portion of the second pusher, and a second suture portion, the second pusher being oriented relative to the first pusher to penetrate body tissue generally opposite from the first pusher, the first suture portion and the second suture portion thereby being adapted to pull together generally opposite walls of said body tissue defining a wound;
   wherein said helical shapes of said distal portions of the first pusher and the second pusher each define an axis, said axes being nonparallel and being angled outward with respect to each other toward said distal ends; wherein an included angle between said axes is an acute angle.

2. The wound closure device according to claim 1, wherein the first pusher and the second pusher rotate in opposite directions.

3. The wound closure device according to claim 1, wherein said helical paths of the first pusher and the second pusher circumferentially overlap each other.

4. The wound closure device according to claim 1, wherein said distal ends of the first pusher and the second pusher are longitudinally offset from each other.

5. The wound closure device according to claim 1, wherein the included angle between said axes is about 8° to about 16°.

6. The wound closure device according to claim 1, wherein the first pusher and the second pusher rotate in opposite directions, said helical paths of the first pusher and the second pusher circumferentially overlap each other.

7. The wound closure device according to claim 1, wherein the first pusher rotates about 180° to about 240° as said first sharp tip penetrates said body tissue and as the first pusher retracts from said body tissue.

8. The wound closure device according to claim 1, wherein the first suture portion is attached to the first sharp tip and the first sharp tip is separable from the first pusher.

9. The wound closure device according to claim 8, wherein the first sharp tip comprises a first catch and said housing comprises a second catch configured to retain the first sharp tip after penetrating said body tissue, the first sharp tip thereby separating from the first pusher as the first pusher is retracted.

10. The wound closure device according to claim 1, wherein the first suture portion is attached to the first sharp tip and the first sharp tip is separable from the first pusher, said housing comprises a second port, the first sharp tip being configured to be received within said second port after penetrating said body tissue, the first sharp tip configured to remain in said second port after penetrating said body tissue, and the first sharp tip is configured to separate from the first pusher as the first pusher is retracted.

11. The wound closure device according to claim 1, wherein the first suture portion moves outward through said first port as the first pusher advances through said body tissue.

12. The wound closure device according to claim 1, wherein the first suture portion extends away from said distal portion of the first pusher along an exterior of said housing.

13. The wound closure device according to claim 1, wherein said distal portion of the first pusher comprises a longitudinal cavity, the first suture portion being disposable within said longitudinal cavity as the first pusher extends through said body tissue.

14. The wound closure device according to claim 13, wherein said distal portion of the first pusher comprises a longitudinal opening along an outer edge thereof in communication with said longitudinal cavity, the first suture portion configured for passing out of said longitudinal cavity through said longitudinal opening as the first pusher is retracted.

15. The wound closure device according to claim 1, wherein said housing comprises a tapered portion, said helical path of the first pusher extending along at least a portion of said tapered portion.

16. The wound closure device according to claim 1, wherein the first pusher and the second pusher each rotate about 180° to about 240° as the first sharp tip and the second sharp tip penetrate said body tissue and as the first pusher and the second pusher retract from said body tissue, the first suture portion is attached to the first sharp tip and the first sharp tip is separable from the first pusher, and the second suture portion is attached to the second sharp tip and the second sharp tip is separable from the second pusher.

17. The wound closure device according to claim 16, wherein said first pusher and said second pusher rotate in opposite directions, and said housing comprises another first port, the second sharp tip being disposed within said housing before penetrating said body tissue, and the second sharp tip and said distal portion of the second pusher configured to move outward through said another first port to penetrate said body tissue.

18. The wound closure device according to claim 17, wherein said housing comprises a second port, the first sharp tip comprises a first catch and said housing comprises a second catch in said second port, said second catch retaining the first sharp tip after penetrating said body tissue, said second catch configured to separate the first sharp tip from the first pusher as the first pusher is retracted, said housing comprises another second port, the second sharp tip comprises another first catch and said housing comprises another second catch in said another second port, said another second catch retaining the second sharp tip after penetrating said body tissue, said another second catch configured to separate the second sharp tip from the second pusher as the second pusher is retracted, said distal portions of the first pusher and the second pusher each comprise a longitudinal cavity with a longitudinal opening along an outer edge thereof, the first suture portion and the second suture portion being disposable within said longitudinal cavities as the first pusher and the second pusher extend through said body tissue, and the first suture portion and the second suture portion passing out of said longitudinal cavities through said longitudinal openings as the first pusher and the second pusher are retracted, and said housing comprises a tapered portion, said helical paths of the first pusher and the second pusher extending along at least a portion of said tapered portion.

\* \* \* \* \*